United States Patent
Vogel et al.

(10) Patent No.: US 6,758,961 B1
(45) Date of Patent: Jul. 6, 2004

(54) POSITIONING AND ELECTROPHYSIOLOGICAL CHARACTERIZATION OF INDIVIDUAL CELLS AND RECONSTITUTED MEMBRANE SYSTEMS ON MICROSTRUCTURED CARRIERS

(75) Inventors: Horst Vogel, Préverenges (CH); Christian Schmidt, Ecublens (CH)

(73) Assignees: Ecole Polytechnique Federale de Lausanne (CH); Cytion SA (CH)

( * ) Notice: Subject to any disclaimer, the term of this patent is extended or adjusted under 35 U.S.C. 154(b) by 0 days.

(21) Appl. No.: 09/581,837

(22) PCT Filed: Jul. 28, 1998

(86) PCT No.: PCT/IB98/01150

§ 371 (c)(1),
(2), (4) Date: Oct. 13, 2000

(87) PCT Pub. No.: WO99/31503

PCT Pub. Date: Jun. 24, 1999

(30) Foreign Application Priority Data

Dec. 17, 1997 (CH) ................................. 2903/97

(51) Int. Cl.[7] .......................................... G01N 33/483
(52) U.S. Cl. ............................ 205/777.5; 204/403.01; 204/403.03; 435/173.4; 435/173.6
(58) Field of Search ................... 204/403.01, 403.03, 204/416; 205/777.5, 778; 435/4, 173.4, 173.6, 287.1, 288.4, 288.7

(56) References Cited

U.S. PATENT DOCUMENTS

| | | |
|---|---|---|
| 4,055,799 A | 10/1977 | Coster et al. |
| 4,062,750 A | 12/1977 | Butler |
| 4,071,315 A | 1/1978 | Chateau |
| 4,128,456 A | 12/1978 | Lee et al. |
| 4,225,410 A | 9/1980 | Pace |
| 4,441,507 A | 4/1984 | Steffin |
| 4,490,216 A | 12/1984 | McConnell |
| 4,510,442 A | 4/1985 | Neher |
| 4,803,154 A | 2/1989 | Uo et al. |
| 4,894,343 A | 1/1990 | Tanaka et al. |
| 4,911,806 A | 3/1990 | Hofmann |
| 4,912,060 A | 3/1990 | Fein |
| 4,952,518 A | 8/1990 | Johnson et al. |
| 5,009,846 A | 4/1991 | Gavet et al. |
| 5,041,266 A | 8/1991 | Fox |

(List continued on next page.)

FOREIGN PATENT DOCUMENTS

| | | |
|---|---|---|
| AU | 75770/91 | 2/1995 |
| AU | 656520 B | 9/1995 |

(List continued on next page.)

OTHER PUBLICATIONS

English abstract for HU 200000996 A1, Illes et al, Nov. 2001.*

McCrone "Microscopy" from Kirk–Othmer, *Encyclopedia of Chemical Technology*, pp. 651, 658–659, 1995.

(List continued on next page.)

Primary Examiner—Kaj K. Olsen
(74) Attorney, Agent, or Firm—Kolisch Hartwell, P.C.

(57) ABSTRACT

The invention relates to a measuring device which permits a very simple positioning of cells and vesicles respective of cell membranes on planar carriers. The invention also relates to a corresponding highly efficient method for the positioning and electric characterization of such membranes with a consistently high signal-to-noise ratio. In addition, statements concerning interactions of substances with lipid membranes respective of materials bonded thereon or therein respective of signal transduction mechanisms connected thereto are possible.

149 Claims, 5 Drawing Sheets

U.S. PATENT DOCUMENTS

| | | |
|---|---|---|
| 5,169,600 A | 12/1992 | Ishizaka et al. |
| 5,187,096 A | 2/1993 | Giaever et al. |
| 5,229,163 A | 7/1993 | Fox |
| 5,234,566 A | 8/1993 | Osman et al. |
| 5,262,128 A | 11/1993 | Leighton et al. |
| 5,378,342 A | 1/1995 | Ikematsu et al. |
| 5,443,955 A | 8/1995 | Cornell et al. |
| 5,506,141 A | 4/1996 | Weinreb et al. |
| 5,508,200 A | 4/1996 | Tiffany et al. |
| 5,510,628 A | 4/1996 | Georger, Jr. et al. |
| 5,563,067 A | 10/1996 | Sugihara et al. |
| 5,605,662 A | 2/1997 | Heller et al. |
| 5,632,957 A | 5/1997 | Heller et al. |
| 5,750,015 A | 5/1998 | Soane et al. |
| 5,780,752 A | 7/1998 | Okubo et al. |
| 5,810,725 A | 9/1998 | Sugihara et al. |
| 5,889,216 A | 3/1999 | Okubo et al. |
| 5,904,824 A | 5/1999 | Oh |
| 5,911,871 A | 6/1999 | Preiss et al. |
| 5,955,352 A | 9/1999 | Inoue et al. |
| 5,958,345 A | 9/1999 | Turner et al. |
| 5,981,268 A | 11/1999 | Kovacs et al. |
| 6,015,714 A | 1/2000 | Baldarelli et al. |
| 6,032,062 A | 2/2000 | Nisch |
| 6,048,722 A | 4/2000 | Farb et al. |
| 6,056,861 A | 5/2000 | Fuhr et al. |
| 6,063,260 A | 5/2000 | Olesen et al. |
| 6,068,818 A | 5/2000 | Ackley et al. |
| 6,093,296 A | 7/2000 | Soane et al. |
| 6,099,803 A | 8/2000 | Ackley et al. |
| 6,103,479 A | 8/2000 | Taylor |
| 6,113,768 A | 9/2000 | Fuhr et al. |
| 6,117,291 A | 9/2000 | Olesen et al. |
| 6,132,582 A | 10/2000 | King et al. |
| 6,143,496 A * | 11/2000 | Brown et al. .................. 435/6 |
| 6,151,519 A | 11/2000 | Sugihara et al. |
| 6,156,181 A | 12/2000 | Parce et al. |
| 6,163,719 A | 12/2000 | Sherman |
| 6,177,000 B1 | 1/2001 | Peterson |
| 6,207,031 B1 | 3/2001 | Adourian et al. |
| 6,225,059 B1 | 5/2001 | Ackley et al. |
| 6,228,326 B1 | 5/2001 | Boxer et al. |
| 6,235,520 B1 | 5/2001 | Malin et al. |
| 6,267,872 B1 | 7/2001 | Akeson et al. |
| 6,277,629 B1 | 8/2001 | Wolf et al. |
| 6,284,113 B1 | 9/2001 | Bjornson et al. |
| 6,287,517 B1 | 9/2001 | Ackley et al. |
| 6,315,940 B1 | 11/2001 | Nisch et al. |
| 6,329,209 B1 | 12/2001 | Wagner et al. |
| 6,355,491 B1 | 3/2002 | Zhou et al. |
| 6,368,851 B1 | 4/2002 | Baumann et al. |
| 6,377,057 B1 | 4/2002 | Borkholder |
| 6,403,367 B1 | 6/2002 | Cheng et al. |
| 6,448,794 B1 | 9/2002 | Cheng et al. |
| 6,461,860 B2 | 10/2002 | Mathes et al. |
| 6,470,226 B1 | 10/2002 | Olesen et al. |
| 6,475,760 B1 | 11/2002 | Baumann et al. |
| 6,475,808 B1 | 11/2002 | Wagner et al. |
| 6,488,829 B1 | 12/2002 | Schroeder et al. |
| 6,596,143 B1 | 7/2003 | Wang et al. |
| 6,630,835 B2 | 10/2003 | Cheng et al. |
| 6,638,743 B2 | 10/2003 | Baumann et al. |
| 2001/0005489 A1 | 6/2001 | Roach et al. |
| 2001/0005774 A1 | 6/2001 | Kato et al. |
| 2001/0045359 A1 | 11/2001 | Cheng et al. |
| 2002/0072103 A1 | 6/2002 | Matsumoto et al. |
| 2002/0076825 A1 | 6/2002 | Cheng et al. |
| 2002/0119579 A1 | 8/2002 | Wagner |
| 2002/0137121 A1 | 9/2002 | Rubinsky et al. |
| 2002/0155586 A1 | 10/2002 | Cheng et al. |
| 2002/0182627 A1 | 12/2002 | Wang et al. |
| 2002/0190732 A1 | 12/2002 | Cheng et al. |
| 2003/0059936 A1 | 3/2003 | Baumann et al. |
| 2003/0070923 A1 | 4/2003 | Schroeder et al. |
| 2003/0121778 A1 | 7/2003 | Dodgson et al. |
| 2003/0134416 A1 | 7/2003 | Yamanishi et al. |
| 2003/0219884 A1 | 11/2003 | Lison et al. |

FOREIGN PATENT DOCUMENTS

| | | |
|---|---|---|
| DE | 19605830 | 2/1997 |
| DE | 19628928 | 1/1998 |
| DE | 19646505 | 5/1998 |
| DE | 19712309 | 5/1998 |
| DE | 19815882 | 10/1999 |
| DE | 19827957 | 12/1999 |
| DE | 19948473 | 4/2001 |
| DE | 19961951 | 6/2001 |
| DE | 10008373 | 9/2001 |
| DE | 10022772 | 11/2001 |
| DE | 10047390 | 4/2002 |
| DE | 10061347 | 6/2002 |
| DE | 20220299 U1 | 5/2003 |
| DE | 10218325 | 11/2003 |
| EP | 0 094 193 A2 | 11/1983 |
| EP | 0299778 | 1/1989 |
| EP | 0299779 | 1/1989 |
| EP | 0162907 B1 | 1/1992 |
| EP | 0639768 | 2/1995 |
| EP | 0962524 | 9/1999 |
| EP | 0960933 | 12/1999 |
| EP | 1035918 | 9/2000 |
| EP | 1040349 | 10/2000 |
| EP | 1178315 | 2/2002 |
| EP | 1203823 | 5/2002 |
| EP | 1333279 | 8/2003 |
| FR | 2659347 | 9/1991 |
| GB | 2360162 | 5/2001 |
| GB | 2355354 | 4/2002 |
| GB | 2 371 626 | 7/2002 |
| JP | 4-204211 | 7/1992 |
| JP | 4-204244 | 7/1992 |
| JP | 4-338240 | 11/1992 |
| JP | 2003-307481 | 10/2003 |
| WO | WO 85/02201 | 5/1985 |
| WO | WO 89/01159 | 2/1989 |
| WO | WO 91/13977 | 9/1991 |
| WO | WO 94/25862 | 11/1994 |
| WO | WO 96/13721 | 5/1996 |
| WO | WO 97/17426 | 5/1997 |
| WO | WO 97/40104 | 10/1997 |
| WO | WO 97/49987 | 12/1997 |
| WO | WO 98/01150 | 1/1998 |
| WO | WO 98/22819 | 5/1998 |
| WO | WO 98/47003 | 10/1998 |
| WO | WO 98/58248 | 12/1998 |
| WO | WO 99/19729 | 4/1999 |
| WO | WO 99/28037 | 6/1999 |
| WO | WO 99/31503 | 6/1999 |
| WO | WO 99/39829 | 8/1999 |
| WO | WO 99/66329 | 12/1999 |
| WO | WO 00/34776 | 6/2000 |
| WO | WO 00/71742 | 11/2000 |
| WO | WO 01/07583 | 2/2001 |
| WO | WO 01/07584 | 2/2001 |
| WO | WO 01/07585 | 2/2001 |
| WO | WO 01/25769 | 4/2001 |
| WO | WO 01/27614 | 4/2001 |
| WO | WO 01/34764 | 5/2001 |
| WO | WO 01/48474 | 7/2001 |
| WO | WO 01/48475 | 7/2001 |
| WO | WO 01/59153 | 8/2001 |

| WO | WO 01/59447 | 8/2001 |
| WO | WO 01/69241 | 9/2001 |
| WO | WO 01/71349 | 9/2001 |
| WO | WO 01/75438 | 10/2001 |
| WO | WO 01/81425 | 11/2001 |
| WO | WO 01/86290 | 11/2001 |
| WO | WO 01/94939 | 12/2001 |
| WO | WO 02/00217 | 1/2002 |
| WO | WO 02/02608 | 1/2002 |
| WO | WO 02/04656 | 1/2002 |
| WO | WO 02/08748 | 1/2002 |
| WO | WO 02/10747 | 2/2002 |
| WO | WO 02/12896 | 2/2002 |
| WO | WO 02/16936 | 2/2002 |
| WO | WO 02/27909 | 4/2002 |
| WO | WO 02/28523 | 4/2002 |
| WO | WO 02/29402 | 4/2002 |
| WO | WO 02/31505 | 4/2002 |
| WO | WO 03/046216 | 6/2002 |
| WO | WO 02/052045 | 7/2002 |
| WO | WO 02/59597 | 8/2002 |
| WO | WO 02/59598 | 8/2002 |
| WO | WO 02/59603 | 8/2002 |
| WO | WO 02/65092 | 8/2002 |
| WO | WO 02/066596 | 8/2002 |
| WO | WO 02/073159 | 9/2002 |
| WO | WO 02/074983 | 9/2002 |
| WO | WO 02/077259 | 10/2002 |
| WO | WO 02/077627 | 10/2002 |
| WO | WO 02/095357 | 11/2002 |
| WO | WO 02/103354 | 12/2002 |
| WO | WO 03/089564 | 10/2003 |
| WO | WO 03/093494 | 11/2003 |

OTHER PUBLICATIONS

*Improved Patch–Clamp Techniques for High–Resolution Current Recording From Cells and Cell–Free Membrane Patches,* Hamill et al., *Pflügers Arch.,* vol. 391, pp. 85–100, 1981.

*Preparation of Large Unilamellar Vesicles,* Hub et al., *FEBS Letters,* vol. 140, No. 2, pp. 254–256, Apr. 1982.

*A Membrane Fusion Strategy for Single–Channel Recordings of Membranes Usually Non–Accessible to Patch–Clamp Pipette Electrodes,* Criado et al., *FEBS Letters,* vol. 224, No. 1, pp. 172–176, Nov. 1987.

*Muscarinic Activation of Ionic Currents Measured by a New Whole–Cell Recording Method,* Horn et al., *Journal of General Physiology,* vol. 92, pp. 145–159, Aug. 1988.

*Single Channel Recordings of Reconstituted Ion Channel Proteins: An Improved Technique,* Keller et al., *Pflügers Arch.,* vol. 411, pp. 94–100, 1988.

*Anti–T2 Monoclonal Antibody Immobilization on Quartz Fibers: Stability and Recognition of T2 Mycotoxin,* Williamson et al., *Analytical Letters,* vol. 22, No. 4, pp. 803–816, 1989.

*Low Access Resistance Perforated Patch Recordings Using Amphotericin B,* Rae et al., *Journal of Neuroscience Methods,* vol. 37, pp. 15–26, 1991.

*Receptor Screening and the Search for New Pharmaceuticals,* Hodgson, *Bio/Technology,* vol. 10, pp. 973–980, Sep. 1992.

*Functional Reconstitution of the Nicotinic Acetylcholine Receptor by CHAPS Dialysis Depends on the Concentrations of Salt, Lipid, and Protein,* Schürholz et al., *Biochemistry,* vol. 31, pp. 5067–5077, 1992.

*Modeling Success and Failure of Langmuir–Blodgett Transfer of Phospholipid Bilayers to Silicon Dioxide,* Osborn et al., *Biophysical Journal,* vol. 68, pp. 1364–1373, Apr. 1995.

*Lipid Vesicle Adsorption Versus Formation of Planar Bilayers on Solid Surfaces,* Nollert et al., *Biophysical Journal,* vol. 69, pp. 1447–1455, Oct. 1995.

*Phenomenology and Kinetics of Lipid Bilayer Spreading on Hydrophilic Surfaces,* Rädler et al., *Langmuir,* vol. 11, No. 11, pp. 4539–4548, 1995.

*A Highly Stable and Selective Biosensor Using Modified Nicotinic Acetylcholine Receptor (nAChR),* Eray et al., *BioSystems,* vol. 35, pp. 183–188, 1995.

*G. Proteins and Regulation of Adenylate Cyuclase (Nobel Lecture),* Gilman, *Angew. Chem. Int. ed. Engl.,* vol. 34, pp. 1406–1419, 1995.

*Signal Transduction: Evolution of an Idea (Nobel Lecture),* Rodbell, *Angew. Chem. Int. Ed. Engl.,* vol. 34, pp. 1420–1428, 1995.

*Shape Change and Physical Properties of Giant Phospholipd Vesicles Prepared in the Presence of an AC Electric Field,* Mathivet et al., *Biophysical Journal,* vol. 70, pp. 1112–1121, Mar. 1996.

*Preparation of Giant Liposomes in Physiological Conditions and Their Characterization Under an Optical Microscope,* Akashi et al., *Biophysical Journal,* vol. 71, pp. 3242–3250, Dec. 1996.

*Preparation of Giant Myelin Vesicles and Proteoliposomes to Register Ionic Channels,* Regueiro et al., *Journal of Neurochemistry,* vol. 67, No. 5, pp. 2146–2154, 1996.

*Critical Dependence of the Solubilization of Lipid Vesicles by the Detergent CHAPS on the Lipid Composition. Functional Reconstitution of the Nicotinic Acetylcholine Receptor Into Preformed Vesicles Above the Critical Micellization Concentration,* Schürholz, *Biophysical Chemistry,* vol. 58, pp. 87–96, 1996.

*A Novel Chloride Channel in Vicia faba Guard CellVacuoles Activated by the Serine/Threonine Kinase, CDPK,* Pei et al., *EMBO Journal,* vol. 15, No. 23, pp. 6564–6574, 1996.

*Single Binding Versus Single Channel Recordings: A New Approach to Study Ionotropic Receptors,* Edelstein et al., *Biochemistry,* vol. 36, No. 45, pp. 13755–17650, 1997.

*Patch Clamp on a Chip,* Sigworth et al., *Biophysical Journal,* vol. 82, pp. 2831–2832, Jun. 2002.

*Effect of Internal Fluoride and Phosphate on Membrane Currents During Intracellular Dialysis of Nerve Cells,* Kostyuk et al., *Nature,* vol. 257, pp. 691–693, Oct. 23, 1975.

*Role of Electrogenic Sodium Pump in Slow Synaptic Inhibition is Re–evaluated,* Kostyuk et al., *Nature,* vol. 267, May 5, 1977.

*Fusion of Phospholipid Vesicles with Planar Phospholipid Bilayer Membranes,* Cohen et al., *J. Gen. Physiol.,* vol. 75, pp. 251–270, Mar. 1980.

*Formation and Properties of Cell–Size Lipid Bilayer Vesicles,* Mueller et al., *Biophysics Journal,* vol. 44, pp. 375–381, Dec. 1983.

*Novel Method of Cell Fusion in Field Constriction Area in Fluid Integrated Circuit,* Masuda et al., *IEEE Trans. IAS,* XP–002181725, pp. 1549–1553, Oct. 1987.

*Current–Voltage Relationships of a Sodium–Sensitive Potassium Channel in the Tonoplast of Chara Corallina,* Bertl, *Journal of Membrane Biology,* vol. 109, pp. 9–19, 1989.

*Optimizing Planar Lipid Bilayer Single–Channel Recordings for High Resolution with Rapid Voltage Steps,* Wonderlin et al., *Biophysics Journal,* vol. 58, pp. 289–297, Aug. 1990.
*Patch Clamp of Cation Channels,* Lewis et al., *Current Topics in Membranes and Transport,* vol. 37, pp. 215–245, 1990.
*Reconstitution of Epithelial Ion Channels,* Bridges et al., *Current Topics in Membranes and Transport,* vol. 37, pp. 283–312, 1990.
*Patch Voltage Clamping with Low–Resistance Seals: Loose Patch Clamp,* Roberts et al., *Methods in Enzymology,* vol. 207, pp. 155–176, 1992.
*Insertion of Ion Channels into Planar Lipid Bilayers by Vesicle Fusion,* Labarca et al., *Methods in Enzymology,* vol. 207, pp. 447–463, 1992.
*Patch Clamp Techniques: An Overview,* Cahalan et al., *Methods in Enzymology,* vol. 207, pp. 3–14, 1992.
*Glass Technology for Patch Clamp Electrodes,* Rae et al., *Methods in Enzymology,* vol. 207, pp. 66–92, 1992.
*Planar Lipid Bilayers on Patch Pipettes: Bilayer Formation and Ion Channels Incorporation,* Ehrlich, *Methods in Enzymology,* vol. 207, pp. 463–470, 1992.
*The Axon Guide for Electrophysiology and Biophysics Laboratory Techniques,* Axon Instruments, Inc., Jun. 1993.
*Molecular Biology of the Cell,* Third Edition, Alberts et al., pp. 178–189, ® 1994.
*Shape Change and Physical Properties of Gian Phospholipid Vesicles Prepared in the Presence of an AC Electric Field,* Mathivet et al., *Biophysical Journal,* vol. 70, pp. 1112–1121, Mar. 1996.
*Ion Channels from Synaptic Vesicle Membrane Fragments Reconstituted into Lipid Bilayers,* Kelly et al., *Biophysical Journal,* vol. 70, pp. 2593–2599, Jun. 1996.
*Investigating Channel Activity,* Aidley et al., *Ion Channels: Molecules in Action,* pp. 33–57, 1996.
*Nystatin/Ergosterol Method for Reconstituting Ion Channels into Planar Lipid Bilayers,* Woodbury, *Methods in Enzymology,* vol. 294, pp. 319–350, 1999.
*Isolation of Transport Vesicles that Deliver Ion Channels to the Cell Surface,* Sattsangi et al., *Methods in Enzymology,* vol. 294, pp. 339–350 (Astract only included), 1999.
*New UC Berkeley "Bionic Chip" Features Living Biological Cell Successfully Merged With Electronic Circuitry,* University of California Berkeley, Press Release, Feb. 25, 2000.
*Researchers Make 'Bionic Chip,'* Edwards, Associated Press, Feb. 25, 2000.
*A Chip–Based Biosensor for the Functional Analysis of Single Ion Channels,* Schmidt et al., *Angew. Chem. Int. Ed. 2000,* vol. 39, No. 17, pp. 3137–3140, 2000.
*Osmotically Evoked Shrinking of Guard–Cell Protoplasts Causes Vesicular Retrieval of Plasma Membrane into the Cytoplasm,* Kubitscheck et al., *Planta,* vol. 210, pp. 423–431, 2000.
*The Lipid Bilayer Concept and its Experimental Realization: From Soap Bubbles, Kitchen Sink, to Bilayer Lipid Membranes,* Tien et al., *Journal of Membrane Science,* vol. 189, pp. 83–117, 2001.
*Neuron Progamming Tutorial #1,* Martin, Internet pp. 1–7, Mar. 3, 2002.
*Introduction to Voltage Clamp and Current Clamp,* Purves, Internet pp. 1–2, Mar. 3, 2002.
*Microfluidics–Based lab–on–a–chip Systems,* Weigl, *IVDT,* pp. 1–6, internet reprint Apr. 11, 2002.
*Patch Clamping Directly Measures Ionic Current,* Sophion Bioscience, Internet pp. 1–2, May 1, 2002.
*Patch Clamp Technique,* Nanion Products, Internet p. 15, May 1, 2002.
*A Microfabricated Chip for the Study of Cell Electroporation,* Huang et al., pp. 1–4, undated.
*Haptotaxis and the Mechanism of Cell Motility,* Carter, *Nature,* pp. 256–261, Jan. 21, 1967.
*Adhesion of Cells to Surfaces Coated with Polylysine,* Mazia et al., *Journal of Cell Biology,* vol. 66, pp. 198–200, 1975.
*The Feynman Lectures on Physics,* Feynman et al., pp. 10–1 through 10–5, © Feb. 1977.
*Perfusion of Oocytes,* Yoshii et al., *Intracellular Perfusion of Excitable Cells,* pp. 77–89, 1984.
*Intracellular Perfusion of Excitable Cells,* Kostyuk et al., pp. 35–51, 1984.
*Controlled Outgrowth of Dissociated Neurons on Patterned Substrates,* Kleinfeld et al., *The Journal of Neuroscience,* vol. 8, No. 11, pp. 4098–4120, Nov. 1988.
*Patterning Self–Assembled Monolayers Using Microcontact Printing: A New Technology for Biosensors?,* Mrksich et al., *TBTech,* vol. 13, pp. 228–235, Jun. 1995.
*Controlling Cell Attachment on Contoured Surfaces with Self–Assembled Monolayers of Alkanethiolates on Gold,* Mrksich et al., *Proc. Natl. Acad. Sci. USA,* vol. 93, pp. 10775–10778, Oct. 1996.

\* cited by examiner

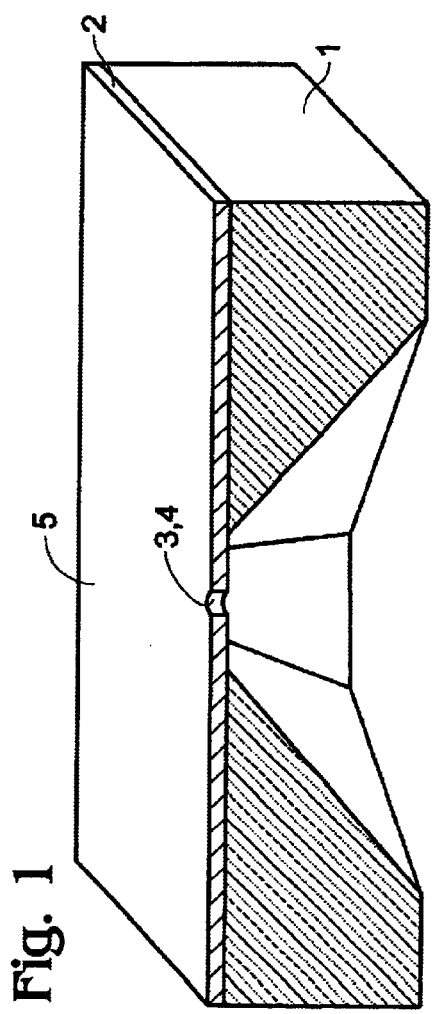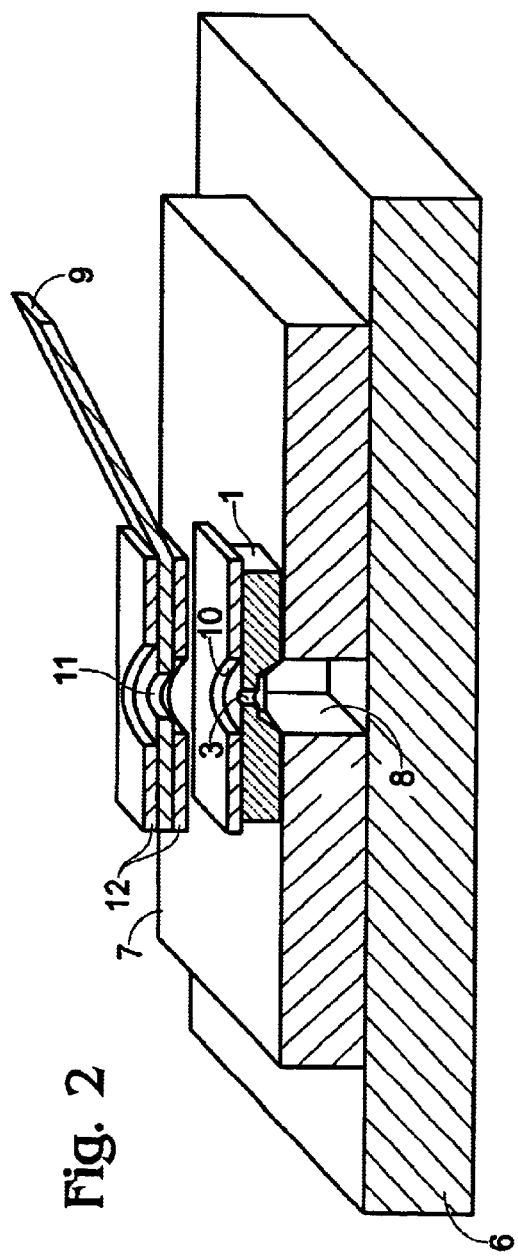
Fig. 1
Fig. 2

US 6,758,961 B1

POSITIONING AND ELECTROPHYSIOLOGICAL CHARACTERIZATION OF INDIVIDUAL CELLS AND RECONSTITUTED MEMBRANE SYSTEMS ON MICROSTRUCTURED CARRIERS

RELATED APPLICATIONS

This Application claims priority of Swiss Application No. 2903/97, which was filed on Dec. 17, 1997.

TECHNICAL AREA

The present invention concerns a measuring arrangement, as well as positioning method for cells and vesicles or lipid membranes, which permits investigations on membranes, especially an electrophysiological method for the investigation of channel-forming proteins and receptors coupled through channel-forming proteins or to channel-forming proteins, by measuring the electrical properties of the channel-forming proteins. Especially, the measurement method according to the invention concerns a (multiarray) patch-clamp method which has the sensitivity and selectivity of the classical patch-clamp technique, but, simultaneously, because of the positioning of biological cells or vesicles on microstructured carriers, also a method according to the invention, simpler preparation of the patch-membranes as well as high signal-noise ratio are achieved. Furthermore, the present invention concerns a measuring arrangement which is suitable both for the positioning as well as for the electrophysiological measurement.

STATE OF THE ART

Many biologically important signal transduction processes, such as nerve conduction, occur on or in the cell membranes. Therefore, it is not surprising that the biological functions of membrane proteins in general and of neuroreceptors in particular are influenced by pharmacologically active compounds (J.-P. Changeux (1993), "Chemical signalling in the brain", *Sci. Am. Nov.*, pages 30 and following; A. G. Gilman (1995), *Angew. Chem. Int. Ed. Engl.* 34: 1406–1428; M. Rodbell (1995), *Angew. Chem. Int. Ed. Engl.* 34: 1420–1428).

The functional understanding of the molecular interactions on receptors, as well as the use of receptors in the screening of active compounds, play a central role in modern drug development. With increasing number of the known target receptors for active ingredients and the rapidly growing number of potential active ingredients from combinatorial chemistry, the demand is increasing for highly sensitive screening methods, which permits analysis of a large number of different substances at high time throughput ("high throughput screening"=HTS).

At the present time, in pharmacological active ingredient screening, still relatively traditional avenues are followed by carrying out time-consuming ligand binding tests and receptor function tests separately (J. Hodgson (1992) *Bio/Technology* 9: 973). On the other hand, membrane proteins such as the receptors coupled to G-proteins and the channel-forming receptors are considered to belong among the most important target proteins for active ingredients (J. Knowles (1997) "Medicines for the new millenium hunting down diseases" *Odyssey*, Vol. 3 (1)). In this connection, still classical patch-clamp methods are used as functional receptor tests. The advantage of this electrophysiological method lies in the fact that the function of the corresponding channel-forming receptor or receptors coupled to channel-forming proteins is directly accessible through the measured electrical properties. The method is highly specific and extremely sensitive—in principle, the channel activity of individual receptor molecules can be measured. Glass micropipettes with an opening diameter typically 1–0.1 $\mu$m are placed on the surface of a biological cell. The membrane surface which is covered by the micropipette is called "patch". When the contact between the glass electrode and the cell membrane surface is sufficiently insulating electrically, then, with the aid of microelectrodes, which are placed on the one hand in the glass pipette and, on the other hand, in the medium opposite the membrane, the ion current through the membrane patch is measured electrically (O. P. Hamill, A. Marty, et al., (1981), "Improved patch-clamp techniques for high-resolution current recording from cells and cell-free membrane patches", *Pflugers Arch* 391 (2): 85–100).

In connection with active ingredients screening, the traditional patch-clamp technique also has decisive disadvantages. Patch-clamp measurements are extremely time-consuming, require specially trained personnel with long experience in this field, and in practice it cannot be used for HTS.

A method and a process have become known from U.S. Pat. No. 4,055,799 for the measurement of the elastic and dielectric properties of diaphragms of living cells. The disclosed device is a container, two electrodes for measuring voltage differences, 2 electrodes for sending out voltage and current pulses, a separating wall, which divides the container into two chambers and which contains one or more holes, a connection for physiological solution and a connection for the introduction of electrolyte solution. For the measurement, the cells are partially in the hole of the separating wall, so that no planar membrane is formed above the opening. EP-A-0 094 193 and WO-A-8 502 201 also disclose the attachment of cells in holes in a carrier, where the attachment is through electrical charging of the carrier, which cannot lead to an inherently accurate positioning of cells or vesicles above a previously defined point (the aperture) with a diameter smaller than the diameter of these objects.

Therefore, the goal of the present invention was to provide a measuring and positioning method which is simple to handle and permits rapid investigation, especially for a (multiarray) patch-clamp method which has the sensitivity and selectivity of the classical patch-clamp technique, but at the same time, eliminates its disadvantages because of the method of automatic positioning of biological cells or vesicles or corresponding lipid membranes by the method according to the invention, as well as the specific surface properties of the measuring arrangement. Furthermore, the present invention concerns a planar positioning and measuring arrangement, which is especially suitable for carrying out the method according to the invention.

DESCRIPTION OF THE INVENTION

The methods according to the invention excel by extreme simplicity in the production of electrically insulating patch membranes, as well as during the subsequent measurement; in combination with modern microtechnological methods, the new technology offers all the possibilities for use in "high throughput screening" (HTS). In addition, the positioning and measuring arrangement as well as the method according to the invention are suitable for combination of electrical and optical measurements, through which new important information about the investigated receptors can be obtained with the planar membrane, and, with the aid of the positioning method according to the invention, today new important information can be obtained on the receptors to be investigated.

The positioning method according to the invention for cells and vesicles or the corresponding lipid membranes is characterized by the fact that a separating wall of electrically insulating material, called carrier below, is arranged between the two electrodes. The carrier has an aperture as well as a surface onto which the membranes are attached. The carrier must not consist of a single piece, but it can be, for example, built up of a holder, onto which the material which is actually relevant for the membrane binding and membrane positioning is attached, or embedded in this material, and that this material has an aperture for the bonding or positioning of the membrane. The attachment of the membrane can be based, for example, on electrostatic interactions between, for example, a negatively charged membrane surface and a positively charged carrier surface. In case the carrier surface as such does not have the desired charge, it can be modified correspondingly. It was shown that cells and vesicles can be positioned very well when they are introduced into the apparatus through an inlet opening of usually 0.2–2 mm diameter, preferably 0.5–1 mm in one electrode or through a tube brought near the apparatus or with the aid of a pipette, where both electrodes, arranged above and below the carrier, have such an electrical potential difference that cells or vesicles are moved electrophoretically onto the aperture. The inlet opening can be of any shape, but usually it is ellipsoidal, especially circular, so that, for example, it can be arranged concentrically above the aperture.

The fixing of the carrier between the electrodes can be done in such a way that a spacer is provided between the particular electrode and the carrier, which, similarly to the carrier itself, is made of electrically insulating material and has channels which are arranged between the aperture and the electrode and are in contact with it. When filled with an electrically conducting solution, these channels can serve as reference chamber or sample chamber. It was found to be expedient when the reference chamber has such a small size that the reference buffer solution contained in it is fixed there by capillary forces. In an extreme case, it is possible to fix the reference volume without physical boundaries and only through capillary forces between the chip and electrode. The sample compartment (the sample compartment) is formed between the chip surface and the addition-electrode. It has no boundaries on the side, but it is held through capillary forces. In the sense of integration of this method, it is also possible to build a sample chamber with side boundaries. The measuring arrangement of the present invention includes embodiments with sample chambers, both without as well as with physical boundaries on the side.

Since, depending on the attempted analysis, it makes sense to bring the membrane into contact with the measuring solution on both sides, addition of an investigated substance can naturally occur on the side that usually serves as reference side. For example, a reference buffer can be introduced in a pasty gel, as a result of which exchange of the liquid outside is possible without changing the composition of the reference buffer stored in the gel. For example, agarose and polyacrylamide can serve as such gels.

The measurement method according to the invention permits especially the measurement of ion channel currents in a reliable and reproducible manner and doing this with a high signal-to-noise ratio. The reason for this is the accurate positioning and subsequent electrically insulated bonding of vesicles, cells or other biological organelles, or membranes of corresponding origin to microstructured openings (also called aperture below), with a diameter $d_M<15$ $\mu$m, preferably <10 $\mu$m, especially 0.3–7 $\mu$m, especially preferably 0.3–5 $\mu$m and quite especially preferably 1–5 $\mu$m. The electrically tight binding of the vesicle or cells or their membranes is achieved through a strong electrostatic attraction between the carrier surface and the membrane surface.

It was found to be expedient for the method according to the invention when the membrane is applied onto a carrier which is as planar as possible. An appropriate carrier can be made of diverse materials; however, it is advantageous for suitable materials that they are preferably not only microscopically flat but that they are relatively flat even on a molecular level. In addition, suitable materials must be inert in the system, nonconducting and preferably chemically modifiable.

Microstructured silicon/silicon oxide or silicon/silicon oxynitride carriers were found to be especially suitable, which, in order to provide good electrical attraction, are coated with a substance that imparts the desired surface charge. For example, polycations are suitable as described by Mazia, Schatten et al. (see D. Mazia, G. Schatten et al., (1975), "Adhesion of cells to surfaces coated with polylysine", *J. Cell. biol.* 66: 198–200). Such polycations are, for example, poly-L-lysine and polyethyleneimine.

In the selection of suitable carrier chip materials themselves, sufficient modifiability of the surface must be ensured, as already mentioned, so that electrostatic or optionally van der Waals or covalent bonding of vesicles or biological cells or corresponding membranes or membrane fragments will become possible. In addition, bonding based on hydrophobic-hydrophilic interactions is possible under certain circumstances (Radler, J., H. Strey, et al., (1995). "Phenomenology and Kinetics of Lipid Bilayer Spreading on Hydrophilic Surfaces", *Langmuir* 11 (11): 4539–4548). Furthermore, the carrier material should be machinable, that is, an aperture or a window of the desired size can be provided in it and focusing of the electrical field onto the aperture should be possible.

As especially suitable carrier is an $Si/SiO_2$ or silicon/silicon oxynitride chip, which can be produced from commercial Si wafers with an oxide layer of a thickness D of usually >200 $\mu$m. Such a carrier can be microstructured easily. For example, using photolithography or, in the case of apertures with d<1.5 $\mu$m, one can use electron beam lithography, and structures can be obtained by anisotropic etching of the silicon in KOH-containing medium as well as reactive ion etching of the quartz layer. In addition to quartz, glass layers, solid or gel-like polymers, etc., are suitable modifiable surfaces. Furthermore, for example, plastomers and elastomers, such as polyimides, polymethyl methacrylates, polycarbonates, silica gels, such as Sylgard, etc., are suitable.

The essential aspect of such structures is the size of the aperture, which should be <15 $\mu$m, mostly <10 $\mu$m, especially <7 $\mu$m and preferably <5 $\mu$m, as well as the size of the window in the surface layer, for example, the quartz, which is preferably <50 $\mu$m; however, in the ideal case, the size of the aperture is reduced in order to permit under certain circumstances (low buffer conductivity) strong focusing of the electrical field onto the aperture, but above all, in order to reduce mechanical stresses (danger of breaking). A strong electrical focusing corresponding to the strong inhomogeneity of the E field (the size of E increases with the approach to the aperture) permits with $F_{electric} \sim E$ (F=force vector, E=electrical field) to obtain a corresponding accurate movement of the vesicle onto the aperture. Naturally, a carrier may have many apertures which are used sequentially or parallel for measurement.

A planar carrier chip, which is equipped with at least one aperture, is introduced between two electrodes. Suitable electrodes are, for example, Ag/AgCl, Pt; as a result of their easy manufacture, however, Ag/AgCl electrodes are preferred. In addition to acting as voltage clamp, the electrodes especially serve for positioning the vesicle or cells or corresponding membrane. The electrodes are usually at a distance of 0.5 to 3 mm, mostly 0.5–1 mm from the carrier, but they can be removed farther. A symmetrical arrangement is preferred, but not necessary.

Through a planar and optically transparent structure, easily realizable in the vertical, for example, using planar point electrodes, or point electrodes arranged outside the verticals going through the aperture, the system described above is suitable for simultaneous electrical and optical (fluorescence) measurements. By using new fluorescence techniques, such as fluorescence correlation spectroscopy and confocal CCD observation, the optical detection of ligand-bonding on individual receptors has become possible. The combination of such optical techniques with the method presented here permits us for the first time to distinguish or resolve ligand-bonding events and channel activities. Thus, for example, important information can be obtained about the stabilization of conformational changes of the receptor by ligand-bonding and on the functional differences of the ligand-bonding sites in the receptor. (J. Edelstein, O. Schaad, J.-P. Changeux (1997), "Single Binding versus Single Channel Recordings: A New Approach to Study Ionotropic Receptors", *Biochemistry* 36; 13755–13760). Such results are important for understanding the mode of action of agonists and antagonists and thus for the development of new drugs.

The many-sided applicability of the measuring device according to the invention can be improved even more by a multiarray design. By microstructuring, various apertures can be applied onto the smallest space, which are either coupled to the same electrodes, or represent separate measurement compartments, since, for example, Ag/AgCl electrodes can also be easily microstructured.

Furthermore, it is possible to couple the measuring arrangement according to the invention with devices for sample addition and sample exchange, for sample separation and for the regulation of the measurements, for example, by connecting the compartment through tubings with a pump system or to a device which functions by hydrostatic pressure differences or by the piezo droplet method or ink-jet method or contact transfer method or electro-osmotic method or temperature-controlled method or capillary electrophoresis (CE) or HPLC (High Pressure Liquid Chromatography).

The measurements can be influenced by the addition of membrane-active substances, for example, by the addition of pore-formers, proteoliposomes and membrane proteins.

The invention will be explained below in more detail with the aid of figures.

BRIEF DESCRIPTION OF THE DRAWINGS

FIG. 1 is a schematic representation of a carrier chip made of $Si/SiO_2$, not to scale and not true to detail.

FIG. 2 is a schematic representation of a measurement structure with plane-parallel electrodes in cross-section, not to scale and not true to detail.

Figure 3:
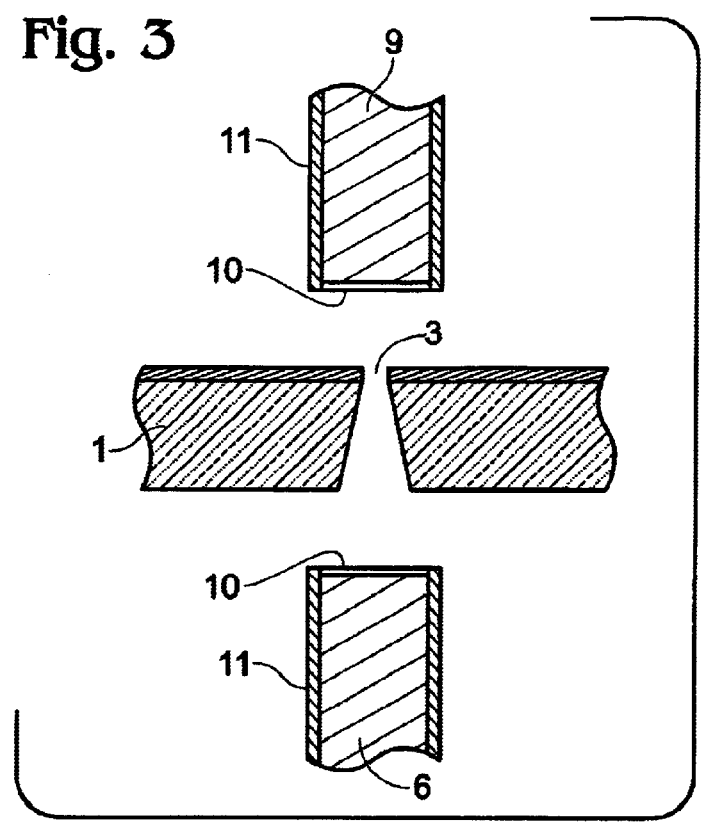
FIG. 3 is a schematic representation of a measurement structure with point or wire electrodes in cross-section, not to scale and not true to detail.
Figure 4:
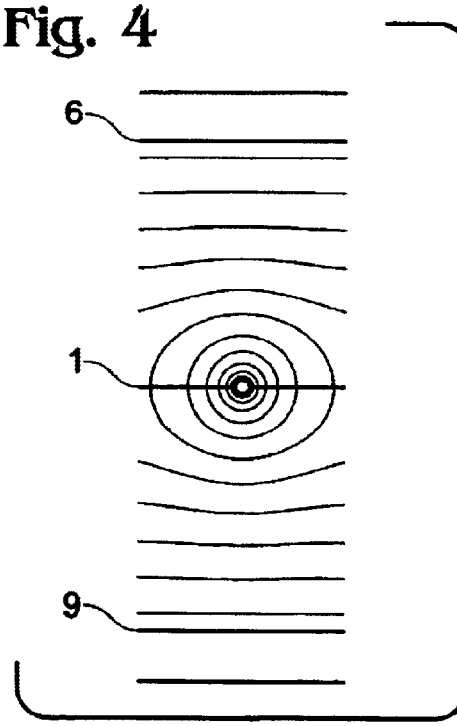
FIG. 4 shows a finite element simulation (FEM) of the electrical field distribution around a chip with 4 μm aperture between parallel electrodes. The following are used as parameters: $c_{buffer}$=10 mM KCl, $d_{aperture}$=4 μm and the distance between chip aperture (4) and electrode (6, 9)=1 mm. The equipotential lines have a distance of 4 mV, where the potential difference between the electrodes is 80 mV. The field-line curve is distorted in this simulation by the assumption of leak currents in the edge region of the carrier chips to become elliptical (normal: circular).
Figure 5A:
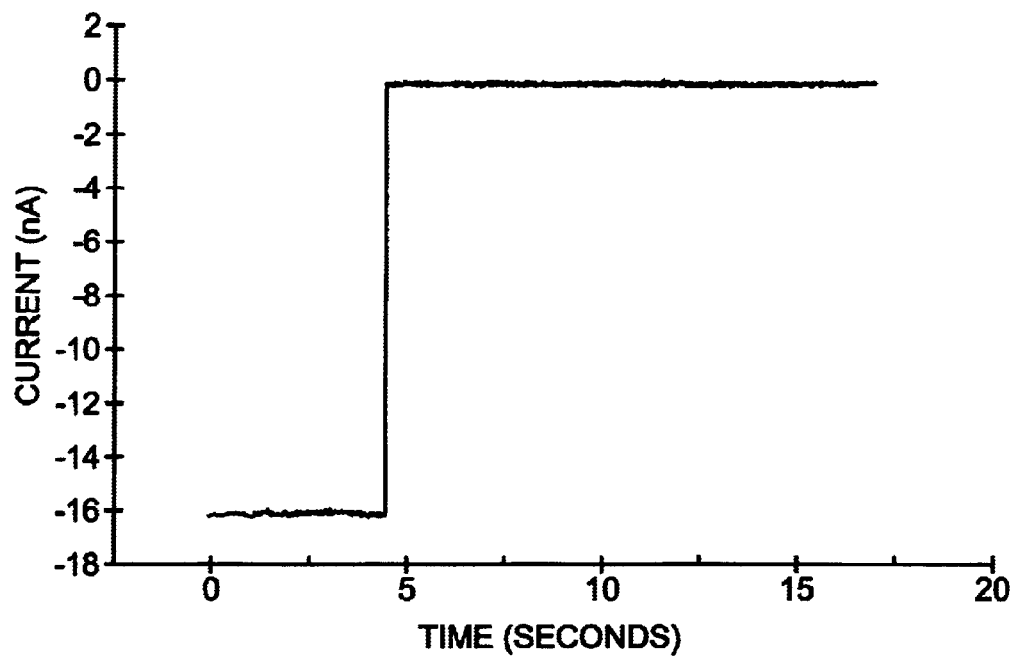
FIG. 5 shows the time course of vesicle bonding and the development of a membrane with very high electrical insulation resistance with an aperture of 4 μm (FIG. 5A) and 7 μm (FIG. 5B), as well as 10 mM KCl, a terminal voltage of −80 mV and PLL-coated $SiO_2$ surface (PLL=poly-L-lysine bromide).
Figure 5B:
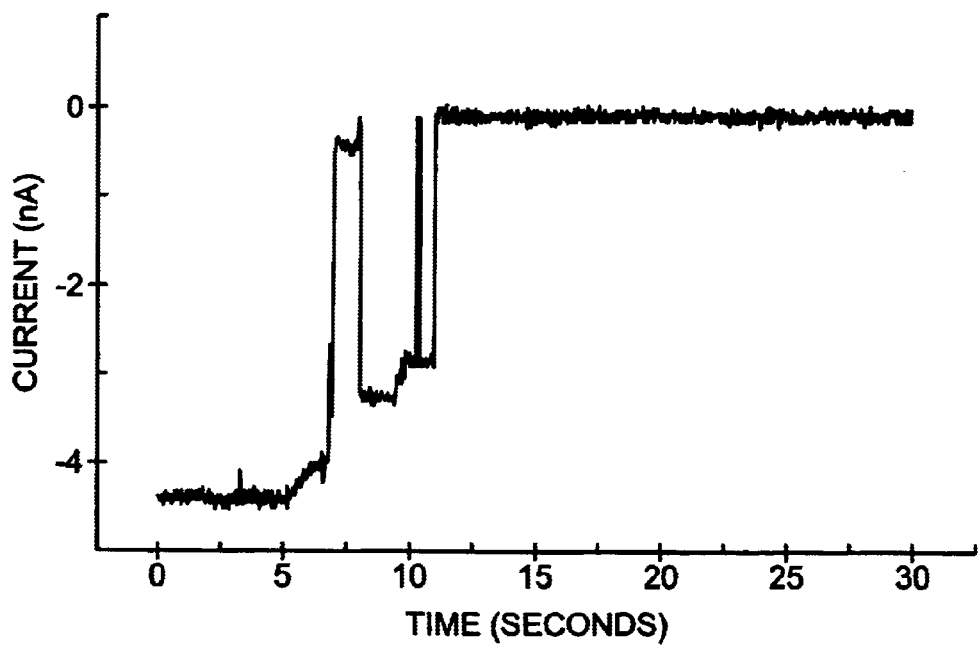

(A) Accidental receptor openings in the absence of ligands with 400 mM KCl and at positive potentials.

(B) 150 seconds after the addition of the nAChR agonist, carbamylcholine (end concentration 20 μM), no receptor openings can be observed any longer (desensitization).

METHOD FOR CARRYING OUT THE INVENTION

The method and the device (measuring arrangement) of the present invention are especially suitable for use in active ingredient screening as a replacement of conventional patch-clamp techniques and as portable biosensors, for example, for environmental analysis. Examples of the measuring arrangements as well as of the areas of application of this will be described in somewhat more detail below.

The measuring arrangement according to the invention has at least two electrodes 6, 9 and separated compartments suitable for holding liquid, and is characterized by the fact that between two redox electrodes 6, 9 of arbitrary shape located opposite and each immersing in at least 1 compartment or being in contact with it, a carrier 1 is located, which contains at least one aperture 3 and separates at least two compartments from one another.

Preferably, on one side or on both sides of carrier 1, there is a means which makes it possible to have liquid addition, liquid storage and, optionally, liquid exchange as well as the addition of cells, vesicles, other biological organelles or parts of these between carrier and electrode. The aperture 3 preferably has a diameter such that, if there is a voltage difference through the chip, mediated by the electrodes 6, 9, an inhomogeneous electrical field is built up around the aperture, which becomes greater as the aperture is approached and near the aperture it is able to move onto this vesicles, cells, cell fragments or biological organelles electrophoretically. Furthermore, preferably carrier 1 has an electrically charged surface 5, which is attractive for biological membranes or has a surface 5, which provides a molecule-specific or multivalent-ion-mediated bonding of cells, vesicles, membrane fragments or biological organelles on it. Such a carrier is, for example, a silicon-carrier chip with applied oxide or oxynitride layer. An electrically charged surface 5 can also be produced by modification, especially with the aid of polycations and/or silanes, for example, amino-silanes, or the carrier may have a layer 2 with electrically charged surface 5. Additionally, before modification of its surface or before its immediate utilization, the carrier 1 can be cleaned in an oxygen plasma and can be made partially or completely hydrophilic.

Based on the special arrangement, it is not necessary for the measuring arrangement according to the invention to have compartments with physical boundaries.

In a preferred embodiment of the measuring arrangement, always one electrode and at least one aperture 3 in carrier 1 are connected to one another through a channel or a chamber 8 in a spacer 7, 10 with the formation of an open or closed compartment.

More than two electrodes 6, 9 and more than aperture 3 may be present in such a way that at least one electrode, for example, a reference electrode, which serves for measurement through more than one aperture 3, or the measuring arrangement may have a carrier 1 with more than one aperture 3 and twice as many electrodes 6, 9 as apertures 3, in such a way that there is always one aperture 3 between two electrodes 6, 9.

Furthermore, the compartments may be coupled through tubings to a pump system or an equipment which operates based on hydrostatic pressure or using the piezo drop method or ink-jet method or a contact transfer method or electro-osmotic method or temperature-control method, in such a way that liquids or samples can be added to arbitrary compartments or can be exchanged within them.

The measuring arrangement according to the invention may also be coupled to an apparatus for producing sample separation, especially by capillary electrophoresis (CE) and HPLC, and serve for analysis of the separated substances, or it can be provided with means which serve for continuous or regular checking of the liquid level in the compartments, as well as with means for controlling an appropriately preset filling parameter.

In another embodiment, the surface 5 of the carrier 1 can be structured in such a way that hydrophilic and hydrophobic areas are produced where the hydrophilic areas are preferably around the aperture.

Such measuring arrangements can be used, for example, for the following measurements, described in detail.

Active Ingredient Screening:

The present invention is eminently suitable for probing a large number of potential ligands, which can be produced in small amounts by combinatorial chemistry. On the other hand, many receptor proteins, especially ligand-controlled and G-protein-coupled receptors are available in very limited amounts. Due to the method according to the invention and the measuring arrangement/measuring device according to the invention, it is possible to operate with very few cells, either directly or after prior isolation and reconstitution of the receptor protein in the vesicles or liquid membranes. Due to the uncomplicated arrangement of the sensor elements in arrays, various substances or receptors can be selected simultaneously at the same time. In addition, there is a possibility to carry out receptor cleaning and reconstitution in lipid vesicles by microchromatography in on-chip containers which can be optionally integrated into the device according to the invention.

Replacement of Conventional Patch-clamp Techniques:

As already mentioned at the outset, conventional patch-clamp techniques represent the foundation for the investigation of the functionality of membrane receptors as well as generally of the change of membrane properties as response to signal- and metabolic processes in cells. If isolated cells of a homogeneous cell population, as is frequently the case, for example, for transformed cells, serve as the object of investigation, the method according to the invention can be at least an equivalent replacement of the patch-clamp technique. Objects to be investigated in this method can be, for example, dissociated neurons and cultivated mammalian cell lines, as well as plant protoplasts.

Portable Biosensors/environmental Analysis:

The excellent mechanical stability of the measuring system according to the invention or its practically automatic membrane build-up permits it use in biosensors. By using suitable transformed cells or receptors reconstituted in vesicles or channel-forming proteins, sensors can be constructed which are sensitive to very different substrates or metabolites. In this way, with very good membrane seal formation, as it is achieved with the aid of the device according to the invention, the sensitivity is mainly dependent only on the bonding constants of the receptor, and, for example, in the case of G-protein-coupled receptors, it can be below one nanomole, and, in the case of ionotropic receptors (for example, 5 HT3, nAChR, $GABA_AR$, glycineR, GluR), can lie in the nanomolar range (North, R. A. (1994), *Ligand and voltage-gated ion channels*, CRC Press; Peroutka, S. J. (1991), *Serotonin receptor subtypes—Basic and clinical aspects*. New York, John Wiley & Sons; Peroutka, S. J. (1994), *G. Protein coupled receptors*, CRC Press; Conley, E. C. (1996), *The ion channel facts book*, Academic Press).

The measurement method according to the invention is based on the following known principle of measurement:

The electrical properties of transmembrane ion channels or of ionotropic receptors are generally characterized by the so-called voltage clamp techniques (for example, classic voltage clamp, patch-clamp and oocyte-voltage-clamp) (see Hamill, Marty et al., 1981 loc. cit.; J. G. Nicholls, A. R. Martin et al., (1992), *From neuron to brain: a cellular and molecular approach to the function of the nervous system*. Sunderland, Mass., Sinauer Associates, Inc.). For this purpose, an electrical potential difference is applied across the membrane which contains the respective ion channel or ion channels, and simultaneously the current necessary for maintaining this difference is analyzed. According to Ohm's law, where $V = I \times R$ or $I = V/R$, this analysis provides information about conductivity and, in relation to this, even though not unequivocally, it provides information about the conformational state of the channel-forming protein. From this, ligand-bonding events, voltage dependences, etc., can be determined.

Since the ion flow through ionotropic membrane proteins is generally very small, with 0.1–50 pA at $V_M = -60$ mV membrane potential, in order to obtain an acceptable signal-to-noise ratio, the variance of the occurring leakage current must lie below the signals to be measured by a factor of 5–10. These leakage currents generally occur between the membrane and its holding and represent the main problem for all voltage-clamp techniques.

The problem can be solved in different ways, for example, by increasing the membrane areas and thus, by summing, providing an increase in the ion current. However, in this case, the specificity is lost, especially in biological systems. Then, generally, no unequivocal or completely artifact-free result can be obtained, for example, when adding a ligand.

The problem of sufficient signal-to-noise ratio can also be solved by building up a very high sealing resistance between membrane and electrode. This principle is used in the present invention. For this purpose, a planar carrier chip with a surface which is strongly adhesive to cells and vesicles is used. This chip separates the two compartments to which different potentials are applied during the measurement, but there is a sub-microscopic opening in its middle. This opening or pore (aperture) is filled with reference buffer solution and is closed electrically insulatingly during the measurement by the strong bonding of cells or vesicles on the surface. This electrically very insulated bonding permits the measurement of even very small ion currents (0.1 pA).

Similar arrangements with lipid membranes which, however, without carrier, satisfy the requirements according to the invention or the modification of the surface according to the invention, could not be used so far for sensitive measurements because of the occurrence of too low sealing resistance of the membrane. These include LB Transfers (R. Coronado and R. Latorre (1983), "Phospholipid bilayers made from monolayers on patch-clamp pipettes", *Biophys. J.* 43(2): 231–6; D. P. Nikolelis and C. G. Siontorou (1995), "Bilayer lipid membranes for flow injection monitoring of acetylcholine, urea and penicillin", *Anal. Chem.* 67(5): 936–44; T. D. Osborn and P. Yager (1995), "Formation of planar solvent-free phospholipid bilayers by Langmuir-Blodgett transfer of monolayers to micromachined apertures in silicon", *Langmuir* 11(1): 8–12; T. D. Osborn and P. Yager (1995), "Modeling success and failure of Langmuir-Blodgett transfer of phospholipid bilayers to silicon dioxide", *Biophys. J.* 68(4): 1364–73 and Vesicle Spreading (P. Nollert, H. Kiefer et al., (1995), "Lipid vesicle adsorption versus formation of planar bilayers on solid surfaces", *Biophys. J.* 69(4): 1447–55; J. Radler, H. Strey, et al., (1995), "Phenomenology and Kinetics of Lipid Bilayer Spreading on Hydrophilic Surfaces", *Langmuir* 11(11): 4539–4548). A miniaturized Black Lipid Membrane (BLM) structure was reported by Eray, Dogan et al., 1995 (see M. Eray, N. S. Dogan et al., (1995), "A highly stable and selective biosensor using modified nicotinic acetylcholine receptor (nAChR)", *Biosystems* 35(2–3): 183–8).

A critical point in the method according to the invention is exact positioning of the cells and vesicles above the pore (aperture). This positioning is achieved by the electrode arrangement and field focusing according to the invention. The distance between the measuring and reference electrode is usually <6 mm, but it can also be greater. Here, the measuring and reference electrodes are each located at a distance of approximately 0.2–3 mm, preferably 0.5–2 mm, especially from 0.5 to 1 mm below and above the carrier chip. A terminal voltage is used which produces an effective electric field for electrophoretic positioning of the vesicle on the aperture. This voltage is not critical, but usually it lies in the range of $V_c$=−30 to −300 mV, especially −60 to −100 mV and especially preferably −60 to −80 mV. As a result of the electrophoretic driving force related to it, vesicles and cells, following the electric field, are moved accurately onto the chip opening. Since the field E is highly inhomogeneous, and increases greatly as the aperture is approached, the vesicles are automatically moved onto the aperture. Since the electrophoretically active field strengths become effective especially near the aperture (distance to aperture <200 µm), the cells/vesicles must be introduced into this region or must arrive there connectively. For this purpose, a hole can be made in the measuring electrode (for example, d<1 mm) opposite the carrier chip opening (aperture).

It is important for all measurements that the opening diameter or aperture diameter be significantly smaller than the diameter of the vesicle or the diameter of the biological cells ($d_{cell}$, $d_{vesicle}$>>$d_{aperture}$). Therefore, for all apertures of d>2 µm, preferably vesicles with diameters d>20 µm are used.

The characteristic electrical properties can be described mathematically as follows:

The thermal noise signal a of a circular lipid membrane is proportional to $R_M^{-1/2}$ (B. Sakmann and E. Neher (1983), *Single-channel recording*, New York, London, Plenum Press):

$$\sigma = \sqrt{\frac{4kTf_c}{R_M}},$$

with $R_M = R_{spec}/(\pi r_M^2)$ it follows:

$$\sigma = r_M \sqrt{\frac{4\pi kTf_c}{R_{spec}}}$$

In these formulas, σ is the effective noise current, r the radius, f the frequency, k the Bolzmann constant, R the resistivity and T the temperature.

It follows from this for a membrane that would be successfully used for measurement purposes that $r_M/\sqrt{R_{spec}}$ must be very small. The minimization of this product can be achieved according to the invention in two different ways, on the one hand, by minimizing the membrane radius $r_M$ and, on the other hand, additionally, through electrically tight closure of the membranes used.

The mechanical stability of the membrane depends on its size. The size of the aperture in the carriers determines the diameter of the membrane to be built. Preferably, the aperture and the window have a comparable diameter. Since the force necessary for deflecting a membrane is proportional to $r_M^{-2}$, it follows for structures with $d_{aperture}$<5 µm and consequently $d_M$<5 µm that the membrane stability is increased extremely in comparison with typical opening widths of $d_{aperture}$>100 µm in the conventional BLM systems.

As already discussed earlier, the carrier for lipid membranes can be produced from various materials, but because of their good and exact machinability, $Si/SiO_2$ and silicon/silicon oxynitride carriers are preferred.

The $Si/SiO_2$ chips, which are used preferably as carrier (FIG. 1) for the lipid membranes, can be produced from commercial Si wafers 1 with an oxide or oxynitride layer thickness 2 of usually >200 nm. Using photolithography or, in the case of apertures 3 of d<1.5 µm, electron-beam lithography, the structures are obtained by anisotropic etching of the silicon in KOH-containing medium as well as by reactive ion etching of the quartz layer. A corresponding carrier is shown schematically in FIG. 1.

In these structures, the size of the aperture is essential, which should be substantially smaller than the vesicles, cells or organelles used. A reduction of the aperture size is advantageous for the formation of a high-quality seal but, on the other hand, it leads to a reduction of the electrical attraction area around the aperture. Apertures from 0.3 to 7 µm give excellent seal probability and quality. The size of the window 4 is reduced to the size of the aperture 3 in the ideal case.

In the selection of suitable carrier chip materials, in addition to machinability, sufficient modifiability of the surface must be paid attention to, so that an electrostatic or covalent bonding with vesicles or biological cells onto it is possible. It was shown here that treatment of the carrier chip in an $O_2$ plasma for several minutes before the actual surface modification contributes greatly to consistent surface properties.

In order to ensure strong adhesion of the vesicles, the surface of the carrier may optionally be coated with an adhesion-improving agent, for example, polycations (see Mazia, Schatten et al., loc. cit., 1975). For physical adsorption, for example, an aqueous solution of polycations, for example, a 0.1% poly-L-lysine bromide solution (Sigma), MW 100,000, can be applied onto the carrier for 2–5 minutes directly before the measurement and then it can be rinsed with the measuring buffer solution. The covalent bonding of peptide polycations is preferably done through activated hydroxyl groups on the quartz surface, for example, with tosyl chloride (triphenylchloromethane) (M. L. Williamson, D. H. Atha et al., (1989), "Anti-T2 monoclonal antibody immobilization on quartz fibers: stability and recognition of T2 mycotoxin", *Analytical Letters* 22(4): 803–816).

By modification of the carrier surface, one achieves attraction of the vesicles with negative surface charge, which is completely sufficient for an electrically highly insulated connection between the membrane and the carrier surface.

The vesicle bonding or cell bonding can also be provided by molecule-specific interactions, for example, biotin-streptavidin or histidine-NTA (histidine nitrilotriacetic acid).

Alternatively to the use of polycations described above, the surface can also be modified by other compounds with cationic properties, in the desired pH range, for example, 4-aminobutyl dimethylmethoxysilane.

Figure 7:
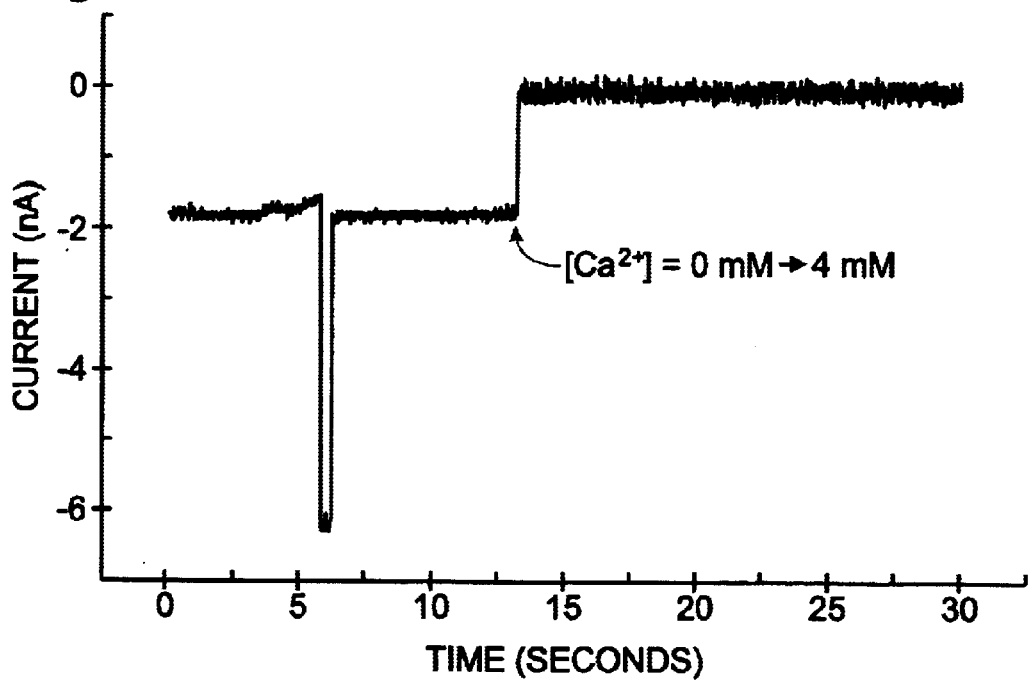
FIG. 7 shows in the current-time diagram that the addition of $Ca^{2+}$ with an end concentration of 4 mM after docking of the vesicles to the unmodified aperture (7 μm) leads to an electrically highly insulated connection between chip surface and vesicle membrane.

Another possibility of the electrically insulating bonding of vesicles to the $SiO_2$ surface is the addition of $Ca^{2+}$ ions to the measuring solution. After setting the vesicle onto the aperture, the $Ca^{2+}$ concentration is increased to >2 mM, and the immediate electrical sealing of the membrane is shown in FIG. 7.

It was shown that a structure with a short distance (D<5 mm) between the electrodes is advantageous in order to obtain a high field strength for the electrophoretic positioning of the vesicles or cells at small voltages ($V_c$<200 mV, especially −200 to 200 mV).

The electrodes are preferably brought to such a distance and the compartments as well as the aperture are filled with buffers or solutions in such a way that, in a spherical but arbitrarily formed area penetrating into the compartment liquid will provide a field strength >100 V/m around the aperture.

In the following, the concrete structure of a measuring system according to the invention with planar electrodes is described (FIG. 2): an electrode 6, for example, a silver plate (for example, purity >99.98% Ag, but lower purity is also possible) with the dimensions of 20×20×2 $mm^3$ is used as sensor carrier and, at the same time, as reference electrode. Using a spacer 7, for example, a 0.5–2 mm thick silicone rubber seal (Sylgard 184, Dow Corning, USA) in the correct distance and parallel, the actual membrane carrier chip 1 is positioned onto this electrode. The spacer has an approximately 1 mm wide and <6 mm long channel (or chamber) 8, which can be, for example, pressed in and which, filled with buffer solution, provides contact between the aperture 3 or membrane and the reference electrode 6, respectively. In order to produce a reference electrode, for example, the preferred Ag/AgCl electrode, the channel is filled, for example, with 1 M HCl and the silver exposed in the channel is chlorinated for 90 seconds, for example, at V=0.8 V. After wetting their bottom side with buffer solution, the carrier chips 1 are placed on the channel 8 filled with reference buffer solution.

During the measurement or during the preparation of the membrane, the measuring solution or vesicle solution is then placed directly on the apertures 3 or window 4 on the top side of the carrier chip 1 or on the top side of the measuring electrode 9, for example, using a volume V of approximately 5–10 µL. In order to minimize disturbances, the region around the aperture 3 can be delineated with a silicone ring 10 (Sylgaard [(Sylgard earlier)] at a distance of, for example, r=1 mm. Together with the meniscus which develops between the chip and measuring electrode, this ring 10 forms the sample compartment. The measuring electrode 9, for example, made of a 0.8 mm thick chlorinated square silver plate (for example, 4×4 $mm^2$), but especially from an annular silver plate (for example, d=2 mm) is positioned especially parallel to the chip surface, preferably at a distance of up to approximately 1 mm, where the opening 11 ($d_{min}$=0.4–1 mm) serving for adding the cells or vesicles and measuring solution located in it and preferably having a funnel shape, is placed preferably exactly concentrically with respect to the microaperture 3 in the carrier chip 1. The measuring electrode can be provided with a spacer 12 on each of the top and bottom, these contributing to the design of the addition opening 11.

By utilizing capillary forces during the filling and storing of the reference and measuring buffer, in spite of its openness, the system is very stable mechanically with regard to filling and storage of the reference and measuring buffer. As a result of the openness, disturbances of the membrane by hydrostatic pressure differences, as they may occur in closed systems, for example, due to temperature differences, are excluded.

Another variation of the embodiment uses point or wire electrodes (FIG. 3): The surface-modified chip 1, which is optionally attached on an especially planar holder, for example, on a glass or teflon holder, is brought between the chlorinated end faces 10 of two silver wires or silver electrodes 6, 9, arranged above and below chip 1, optionally provided on the outside (with the exception of the end faces) with a protecting layer 11, especially a teflon layer, these having, for example, a diameter d=0.1–2 mm (without protecting layer) (distance between electrode 6 and electrode 9, for example, 4 mm). Buffer solution is placed on both sides of the chip using a pipette or tubes brought near to the chip or in one of the sampling handling systems listed below, and the buffer solution is kept between chip and electrode by capillary forces. After offset calibration, an application of a suitable voltage of usually V=−60 to −100 mV, the vesicles/cells are added with a pipette or another tubing or with the sample-handling system listed below to the modified side of the chip. Bonding of the vesicles and development of membrane are followed with the aid of the change of the electrical parameters.

The generally described measuring arrangement, as well as the practical examples described in detail are mainly suitable for integrated systems which are expanded with a sample-handling system. These include liquid-transport systems, which are based, for example, on the use of pumps, hydrostatic pressure differences, electro-osmotic, piezoelectric and temperature effects or mechanical shifting of defined liquid volumes into and/or out of the liquid compartments of the described structure. At the same time, simple parallelizing of the described structure is possible either on a multiaperture chip or with several carrier chips with one aperture.

Large unilamellar vesicles (Giant Unilamellar Vesicles, GUV), which are suitable as membranes, can be produced using the hydratation method (H. H. Hub, U. Zimmermann et al., (1982), "Preparation of large unilamellar vesicles", FEBS Lett. 140(2): 254–256; P. Mueller, T. F. Chien, et al., (1983), "Formation and properties of cell-size lipid bilayer vesicles", Biophys. J. 44(3): 375–81; K. Akashi, H. Miyata, et al., (1996), "Preparation of giant liposomes in physiological conditions and their characterization under an optical microscope", Biophys. J. 71(6): 3242–50). This method, with appropriate modification, also permits the production of proteoliposomes (M. Criado and B. U. Keller (1987), "A membrane fusion strategy for single-channel recordings of membranes usually inaccessible to patch-clamp pipette electrodes", FEBS. Lett. 224(1): 172–6; B. U. Keller, B. Hedrich et al., (1988), "Single channel recordings of reconstituted ion channel proteins: an improved technique", Pflugers Arch 411(1): 94–100).

In order to provide electrically insulating bonding of the vesicle to the chip, a net charging of the vesicle surface, which is opposite to that of the carrier surface, is required. The vesicle surface can be negatively charged, for example, using palmitoyloleyl phosphatidyl glycerol (POPG), in order to provide as physiological conditions as possible for the proteins that are incorporated in the membrane.

After positioning, cells or vesicles can be broken down, for example, by handling with hypotonic medium, for example, pure water, in case they do not burst by themselves.

The measuring structures of the planar type according to the invention are suitable, especially for use for "perforated patch" techniques because of the short diffusion times (R. Horn and A. Marty (1988), "Muscarinic activation of ionic currents measured by a new whole-cell recording method", J. Gen. Physiol. 92(2): 145–59; J. Rae, K. Cooper et al., (1991), "Low access-resistance perforated patch recordings using amphotericin B", J. Neurosci. Methods, 37(1): 15–26). In these techniques, electrical bonding to the inside of the cell (cytosol) is achieved by permeabilizing the membrane spots that normally adhere to the glass pipette with a pore-forming antibiotic. An advantage of this technique is that the cytosol is not washed out with the measuring buffer solution while permitting electrical access simultaneously.

According to the invention, a pore former, for example, amphotericin B or nystatin can be introduced into the reference compartment, after a biological cell, or under special circumstances, vesicle also (when their mechanical stability must be sufficiently high) is bonded to the top side of the aperture. The rate of perforation of the membrane patch above the aperture is significantly higher than in the comparable patch-clamp technique.

In addition, even when the membrane patch is destroyed, analogously to the whole cell patch-clamp technique (WCRT), a simple addition of larger proteins via the reference solution into the cytoplasm is possible. The reason for this is the planar structure of the measuring system, which permits an essentially faster diffusion in comparison to WCRT of large macromolecules into the cytosol or inside the vesicle (Z. M. Pei, J. M. Ward et al., (1996), "A novel chloride channel in Vicia faba guard cell vacuoles activated by the serine/threonine kinase, CDPK", EMBO J. 15(23): 6564–74).

The measurement arrangement according to the invention or the positioning method according to the invention have very broad possibilities of application. In addition to the possible applications already discussed above, they can also serve for the separation or size analysis of vesicles or cells, for the positioning of cells, for example, for pure optical investigations or microinjections. The system especially permits direct functional analysis of ionotropic membrane proteins, for example, in ligand-binding studies. In combination with the simple structure of the reproducibility of the results and mechanical stability of the membrane sections, it is also especially suitable for biosensors in the screening area and represents here a cost-saving and time-saving alternative in comparison to patch-clamp techniques. The simple parallelizability of the system makes it, in principle, also suitable for HTS.

The investigations can be carried out using cells and vesicles, but also cell fragments, cellular organelles and lipid membranes.

The method permits recording of the membrane resistance with good signal-to-noise ratio.

In the method according to the invention, the measuring solution or the reference solution or both solutions can be replaced by another solution or a substance to be analyzed can be added to the solution on the measurement and/or reference side, for example, a pore former, which can be added to one or both compartments, with the goal of increasing the electrical conductivity or the permeability of the membrane to certain ions, or proteolipo-somes of arbitrary size can be added, with the goal of using them with the membranes through aperture 3, and thus making any arbitrary membrane proteins contained in them accessible to electrical or optical measurements. After construction of a membrane, membrane proteins can be incorporated in these through aperture (3).

The method can also be carried out in such a way that an apparatus used, which is designed so that the membrane located above aperture 3 is accessible to optical measurements, especially fluorescence measurements, and then these can be carried out on it.

Several apertures 3 can also be used on a carrier and the measurements can be done above at least two apertures 3 sequentially and/or parallel and/or in such a way that all or several electrodes on one side of carrier 1 have a common electrical potential or are combined to one electrode.

The method will now be explained with the aid of examples. These must not be regarded so that they limit the extent of the invention in any way.

EXAMPLES

Vesicle-formation and Size Separation

Asolectin (Fluka) or Eilecithin (EPC), 100 µL, 50 µL of palmitoyloleyl phosphatidyl glycerol (POPG), 3 µL of dipalmitoyl phosphatidyl ethanolamine-rhodamine (DPPE-rhoda-mine) (Molecular Probes, (USA) (all 10 mg/mL in chloroform, Avanti Polar Lipids) and 70 µL of methanol were dried in a rotary evaporator (Büichi Rotavapor R-114) at a reduced pressure of 400 mmHg in a 10 mL round-bottom flask to form a film. After incubation in vacuum for 1 hour, 10 mL of $H_2O$ or 10 mL of a buffer solution with <150 mM KCl and/or <600 mM sucrose or, preferably, sorbitol were added. The vesicles formed in this process appeared as almost transparent clouds after about 16 h at 37° C. The vesicles were aspirated with a 1 mL pipette and, after (optional) addition of sodium azide ($NaN_3$ end concentration 0.2 weight %) were stored at 4° C. till further use.

The preparation of lipid vesicles according to this method give mostly "greater than 90%", unilamellar vesicles up to a size of 250 μm. In particular, in a dual-label fluorescence experiment, the number of small vesicles (d<5μm) was highly reduced in comparison to the unpurified solution after 24 hours of cleaning. A part of the vesicles contained other smaller vesicles but these were not relevant for formation of the membrane. The use of purified vesicles to build up electrically insulating membranes that close the surface require the separation of all vesicles and lipid impurities, which were smaller than 10 μm. If the separation is insufficient, repulsive effects occur in the neighborhood of the aperture, by the bonding of smaller vesicles, which prevented the electrically insulating closure of the aperture by the large vesicles (>10 μm). The vesicles were separated according to size by dialysis through a nylon net with 20 μm pore size for >20 h; if necessary, the fluidity of the vesicle membrane can be lowered with a corresponding lipid composition by lowering the temperature to $\leq 4°$ C., especially 1° C. The unilamellarity of the vesicle membrane can be demonstrated in a suitable preparation by addition of alamethicin (see R. B. Gennis (1989), *Biomembranes: molecular structure and function*. New York, Berlin, Heidelberg, Springer Verlag) (FIG. 8) and supported by confocal microscopic analyses.

Electrophoretic Positioning of the Vesicle

Variant 1:

Before each measurement, the offset voltage $V_{offset}$ between the electrodes was corrected. For this purpose, 5 μL buffer solution was placed directly on the aperture and then the measuring electrode was approached to the chip surface to 1 mm. After the development of a liquid meniscus between chip surface and electrode, the offset voltage and capacity of the system were compensated.

A vesicle-containing dispersion, 10 μl, was then placed on the top side of the measuring electrode, where the vesicles could be sedimented through the circular opening located in the measuring electrode.

Vesicles which move through the opening of the measuring electrode were accelerated directly onto the aperture under the influence of the electrical field corresponding to the applied electrode voltage $V_M$=−50 to −80 mV. The achieved focusing, measured on the number of vesicle entries through the aperture in the case of unmodified surfaces is dependent on the window size (the part of the $SiO_2$ layer freed by etching is called window. The vesicle throughput was clearly increased in the presence of small $SiO_2$ windows (<45×45 μm²).

Variant 2:

Before each measurement, the offset voltage $V_{offset}$ between the electrode was corrected. For this purpose, after the addition of 5 μL of buffer solution between chip and measuring electrode or reference electrodes, the voltage at which the current flow disappears was determined, that is, $I(V_{offset})$=0 pA.

A vesicle-containing dispersion, 3 μL, was then introduced into the measuring compartment near the aperture, where the vesicle could be sedimented through the circular opening in the measuring electrode, in the case of a plane-parallel electrode arrangement. Vesicles which came near the aperture (<200 μM) in the area of very high field strength (up to several kV), were accelerated directly onto the aperture corresponding to the course of the electric field and, after bonding to the chip surface in an electrically insulating manner, were analyzed electrically.

The electrical positioning described in Variants 1 and 2 was superior to the gravitational sedimentation of cells and vesicles, which was also tested, with regard to the following points: the necessary number of vesicles or cells, the total velocity of membrane formation and probability of successful membrane build-up or cell binding.

Vesicle Binding and Adsorption on Modified $SiO_2$ Surfaces

The bonding of the vesicles described above on polylysine-modified $SiO_2$ surfaces was investigated. This was very strong and occurred after the corresponding approach in less than 0.5 sec. The probability of a successful and electrically insulating positioning depended greatly on the aperture size, on the size of the $SiO_2$ window, as well as on the number, size and size distribution of the vesicles. Carrier chips with apertures $d_{aperture}$<2 μm and windows <40 μm gave a probability of >90% (n>15, where n is the number of experiments) of electrically insulating membrane closures in combination with suspensions of vesicles with $d_{vesicle}$>40 μm. Low fluctuations in the development of insulating aperture closures from chip to chip and for different vesicle suspensions lead to the conclusion that an increase in the number of usable aperture closures could be observed if the aperture width were reduced further or if more highly purified vesicle suspensions were employed.

In the bonding of the vesicles on the surface, these were pulled out to completely flat structures. The membrane of the vesicle was marked with 0.5% rhodamine (red) and the insides of the vesicles were marked with carboxyfluorescein (green). The disappearance of all carboxyfluorescein emission (a color photograph shows exclusively the red color of the rhodamine) indicates the release of carboxyfluorescein and thus to the bursting of the vesicle and unilamellarity of these membranes. The very high membrane insulating resistance measured on the carrier chips, namely $R_M$>6.4 GΩ (n=26) in symmetrical 85 mM KCl indicates the development of lipid membranes which are largely free from electrical defects. The fusion process and the fusion result of the vesicle on polylysine-coated glass were investigated with a confocal microscope (LSM 510, Zeiss Jena, Germany).

In an analogous measurement series in symmetrical 10 mM KCl, the bonding of the vesicles after corresponding approach occurred in less than 0.2 sec. with a probability of >70% (n>15) and a membrane resistance of $R_M$>10 GΩ was measured.

Electrical Parameters of the Lipid Membranes

The resistance of the measuring structure, which was determined mainly by the aperture, was measured before each fusion of a vesicle with modified surface. Depending on the size of the aperture, this ranged up to 1 MΩ (usually smaller than 450 kΩ) in 85 mM KCl. Larger resistances were evaluated as artifacts, such as the inclusion of air bubbles under the aperture.

The membranes formed above the aperture during vesicle fusion or cell binding had a resistance of $R_M$>6.4 GΩ at the same ion concentration. Thus, the capacitance of the carrier chip of a few pF was altered insignificantly.

In an experiment in 1 mM KCl carried out analogously, the resistance of the measuring structure was also determined up to the usual 1 MΩ, depending on the aperture size. At the same ion concentration, the resistivity of the membranes formed above the aperture was usually $R_M$>40 Ω and in 10 mM KCl, it was usually $R_M$>10 GΩ. In these experiments, too, the capacitance of the carrier chip, 160–280 pF, changed insignificantly.

Vesicle Passage Through Micrometer Pores

Figure 6:
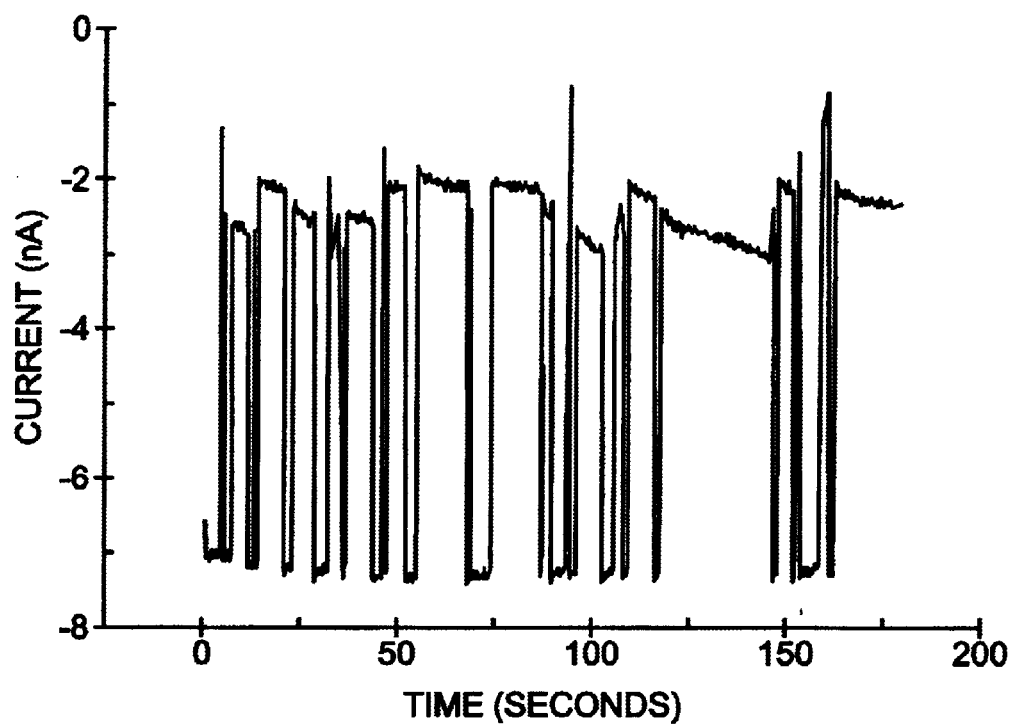
FIG. 6 shows the passage of vesicles through an aperture of 7 μm as modulation in the current-time diagram at a constant terminal voltage of $V_c$=−80 mV.

In the presence of negatively charged surfaces, such as unmodified $SiO_2$ layers or vesicles fused around the aperture, the passage of vesicles through the aperture could be observed based on the resistivity changes (FIG. 6). In order to check artifacts, the voltage was reversed, whereupon no modulation of the resistance was observed.

When the vesicle passages take up to 18 sec, one can conclude that passage of very large vesicles with sufficiently fluid membranes occurred. Especially, when using vesicle populations with d>50 μm (n=4, where n is the number of measurements) and with an aperture of d=7 μm, an almost exclusive variation of the passage time with fixed amplitude changes could be observed as a function of the vesicle size. It can be concluded from this that when vesicles pass through the aperture, they are pulled into tube-like structures with defined diameter and closed surface. The size of the vesicle, which is reflected in the length of the tube, is accessible as the amplitude duration.

In this way, by analysis of the typical passage time for large vesicles ($d_{vesicle}$>>$d_{aperture}$) and the typical resistivity amplitude change for small vesicles ($d_{vesicle}$–$d_{aperture}$) the size composition of the vesicles in a solution can be determined. Thus, this method also opens the possibility of analyzing the populations of vesicles and cells themselves.

Observation of Alamethicin Pores and Nicotinic Acetylcholine Receptors

Figure 8:
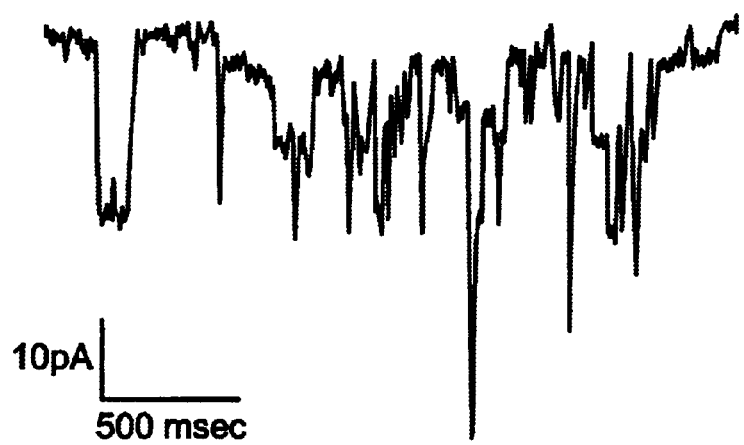
FIG. 8 shows the time- and voltage-dependent switching of alamethicin pores in a membrane produced on the chip ($C_{alamethicin}$=0.1 μg/mL in 85 mM KCl) at negative potentials.
Figure 9A:
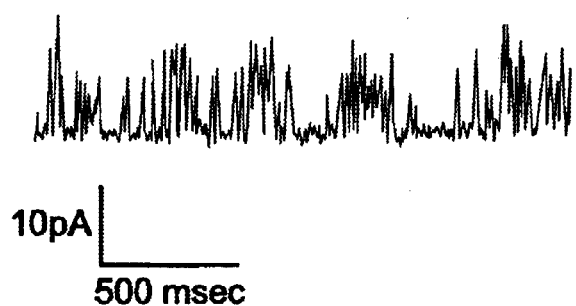
FIG. 9 gives the changes of the membrane resistance of a membrane produced on an $Si/SiO_2$ carrier chip after fusion with vesicles containing nAChR (nicotinic acetylcholine receptor).
Figure 9B:
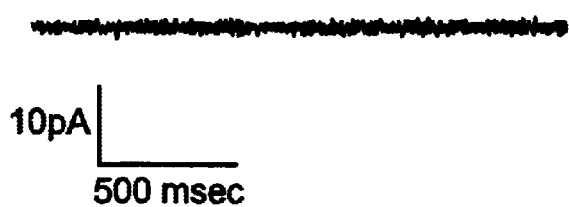

In order to verify the biological functioning of the system according to the invention, after forming a membrane above the aperture in 85 mM KCl, alamethicin (end concentration in the buffer 0.1 μg/mL) was introduced into the measuring compartment (R. B. Gennis (1989), *Biomembranes: molecular structure and function*, New York, Berlin, Heidelberg, Springer Verlag). The occurrence of the current fluctuations (amplitudes and residence times) typical for alamethicin, corresponding to conductivities of about 600 pS in the alamethicin pores, indicates the functionability and high sensitivity of the system (FIG. 8). Similarly, receptor proteins, for example, nAChR, can be introduced into the membrane via fusion with small vesicles (small, medium and large unilamellar vesicles), the fusion being mediated, for example, with $Ca^{2+}$, and can be measured. For this purpose, the nAChR was purified and reconstituted in the vesicle according to Schurholz (Schiürholz, T., J. Kehne, et al., (1992), "Functional reconstitution of the nicotinic acetylcholine receptor by CHAPS dialysis depends on the concentrations of salt, lipid and protein", *Biochemistry* 31(21): 5067–77; Schüirholz, T. (1996), "Critical dependence of the solubilization of lipid vesicles by the detergent CHAPS on the lipid composition. Functional reconstitution of the nicotinic acetylcholine receptor into preformed vesicles above the critical micellization concentration", *Biophys. Chem.* 58(1–2): 87–96). These vesicles were added into the measuring compartment and, by increasing the $Ca^{2+}$ concentration of the sample chamber to >1 mM and, optionally supported by subsequent temporary build-up of an osmotic gradient (see: Eray, Dogan et al., 1995 loc. cit.), were fused with the membrane. In the absence of agonists, typical receptor opening events were recorded (FIG. 9A), which, after the addition of carbamylcholine (20 μM end concentration) largely disappeared within a short time (t<100 sec) (FIG. 9B, Desensitization).

The Bonding of Cells

When substituting the vesicle by biological cells, these can be positioned analogously to the vesicles used and characterized electrically. By supporting the cell membrane through the cytoskeleton, there is no automatic placement of the cells. Thus, after binding of the cell to the chip surface, a configuration similar to the Cell Attached Technique (CAT, Hamill, Marty et al, loc. cit., 1981) is achieved. A prerequisite for noise-free measurement is here above all a relatively smooth membrane surface. Thus, for example, when using plant cells, the cell wall must absolutely be removed.

Starting from the CAT, one can carry out electrical measurements over the entire cell membrane, for example, by electrical destruction of the membrane patches above the aperture (Whole Cell Recording). The addition of pore formers, for example, amphotericin B or nystatin, to the reference compartment and subsequent permeabilization of the membrane patches above the aperture, whole cell measurements can also be performed (perforated patch technique).

Furthermore, by lysis of the cells, recording of the individual channel events in the so-called inside-out configuration is possible, in which the cytosolic membrane side is exposed to the measuring solution.

What is claimed is:

1. A method for analyzing membranous samples, comprising:
    selecting a measuring arrangement, comprising:
        (i) a carrier having at least one aperture,
        (ii) at least two fluid compartments, separated by the carrier, each fluid compartment connected to at least one of the other fluid compartments via at least one of the apertures, and
        (iii) at least two electrodes, each electrode being in electrical contact with at least one of the fluid compartments;
    introducing a sample into one of the fluid compartments;
    applying a voltage between at least two of the electrodes to generate an electric field in the compartment containing the sample;
    moving the sample onto the aperture, under the influence of the electric field;
    sealing the sample across the aperture;
    adding a pore former to at least one fluid compartment to increase the electrical conductivity or permeability of at least a portion of the sample toward certain ions; and
    measuring at least one of an electrical potential and a current across at least a portion of the sample, after the sample is moved to and sealed across the aperture.

2. The method of claim 1, wherein the step of adding a pore former includes adding the pore former to the fluid compartment containing the sample.

3. The method of claim 1, wherein the step of adding a pore former includes adding the pore former to a fluid compartment that is connected to the fluid compartment containing the sample via the aperture across which the sample is sealed.

4. The method of claim 1, wherein the pore former is selected from the group consisting of amphotericin B and nystatin.

5. The method of claim 1, wherein the step of adding a pore former is performed after the steps of moving the sample and sealing the sample.

6. The method of claim 1, further comprising replacing a solution in at least one fluid compartment with another solution.

7. The method of claim 1, further comprising adding a substance to be analyzed to a solution in at least one fluid compartment.

8. The method of claim 1, further comprising:
adding a proteoliposome to the fluid compartment containing the sample; and
fusing the proteoliposome with the sample.

9. The method of claim 1, further comprising incorporating membrane proteins into the sample, after the sample is moved to the aperture.

10. The method of claim 9, wherein the membrane proteins are selected from the group consisting of ligand-controlled receptors and G-protein-coupled receptors.

11. The method of claim 1, further comprising carrying out an optical measurement on the sample.

12. The method of claim 11, wherein the optical measurement is a fluorescence measurement.

13. The method of claim 1, the measuring arrangement including at least two apertures and at least three fluid compartments, further comprising repeating the steps of introducing, applying, moving, sealing, and adding, such that two samples are sealed across a corresponding two apertures in the measuring arrangement.

14. The method of claim 13, further comprising repeating the step of measuring for each of the two samples, wherein the step of measuring is performed sequentially over the two samples.

15. The method of claim 13, further comprising repeating the step of measuring for each of the two samples, wherein the step of measuring is performed in parallel over the two samples.

16. The method of claim 13, the measuring arrangement further including more than two electrodes, wherein the electrodes on one side of the carrier have a common electrical potential.

17. The method of claim 13, the measuring arrangement further including more than two electrodes, wherein the electrodes on one side of the carrier are combined to form one electrode.

18. The method of claim 13, the measuring arrangement further including more than two electrodes, wherein at least one electrode serves for measurement over more than one aperture.

19. The method of claim 13, the measuring arrangement having more than one aperture and twice as many electrodes as apertures, wherein there is always one aperture between two electrodes.

20. The method of claim 1, further comprising adding, exchanging, or regulating fluid or samples on one or both sides of the carrier with the aid of a pump system.

21. The method of claim 1, further comprising adding, exchanging, or regulating fluid or samples on one or both sides of the carrier with the aid of hydrostatic pressure.

22. The method of claim 1, further comprising adding, exchanging, or regulating fluid or samples on one or both sides of the carrier with the aid of a contact transfer method.

23. The method of claim 1, further comprising adding, exchanging, or regulating fluid or samples on one or both sides of the carrier with the aid of an electro-osmotic method.

24. The method of claim 1, further comprising adding, exchanging, or regulating fluid or samples on one or both sides of the carrier with the aid of at least one of a piezo drop method, an ink jet method, and a temperature-controlled method.

25. The method of claim 1, further comprising checking the fluid level in at least one compartment.

26. The method of claim 25, wherein the step of checking is performed continuously or regularly.

27. The method of claim 25, further comprising correcting the fluid level corresponding to a preset filling parameter.

28. The method of claim 1, further comprising modifying at least one of the sample and the carrier to enhance binding between the sample and the carrier.

29. The method of claim 28, wherein the step of modifying includes treating at least one of the sample and the carrier to enhance electrostatic interactions.

30. The method of claim 28, wherein the step of modifying includes treating at least one of the sample and the carrier to enhance molecule-specific interactions.

31. The method of claim 28, wherein the step of modifying includes treating at least one of the sample and the carrier to enhance multivalent-ion-mediated interactions.

32. The method of claim 31, wherein the step of treating includes adding $Ca^{2+}$ to the sample medium.

33. The method of claim 28, wherein the step of modifying includes treating at least one of the sample and the carrier to enhance hydrophilic/hydrophobic interactions.

34. The method of claim 1, further comprising cleaning the carrier in a plasma, before the step of introducing a sample.

35. The method of claim 1, further comprising the step of purifying the sample prior to the steps of adding a sample and applying an electrical potential difference.

36. The method of claim 35, wherein the step of purifying the sample includes separating members of the sample according to size.

37. The method of claim 1, wherein the step of introducing a sample further includes introducing the sample into the compartment through an inlet opening arranged above the aperture.

38. The method of claim 1, wherein the step of moving the sample further includes moving the sample to near the aperture by at least one of convection and sedimentation.

39. The method of claim 1, wherein the step of moving the sample further includes moving the sample electrophoretically.

40. The method of claim 1, wherein the carrier is electrically insulating.

41. The method of claim 1, wherein the carrier is formed at least in part of plastic.

42. The method of claim 1, wherein the carrier is formed at least in part of silicon.

43. The method of claim 42, wherein the carrier includes an applied oxide or oxynitride layer.

44. The method of claim 1, wherein the carrier is formed at least in part of glass.

45. The method of claim 1, wherein the voltage applied between the electrodes during the step of applying a voltage is in a range between about −200 mV and about +200 mV.

46. The method of claim 1, wherein the step of applying a voltage leads to the development of an inhomogeneous electric field in the compartment containing the sample.

47. The method of claim 46, wherein the inhomogeneous electric field is larger closer to the aperture than farther from the aperture.

48. The method of claim 1, wherein the strength of the electric field generated during the step of applying a voltage is at least about 100 V/m adjacent the aperture.

49. The method of claim 1, wherein the sample is selected from the group consisting of cells, biological organelles, and fragments thereof.

50. The method of claim 1, wherein the sample is selected from the group consisting of vesicles, proteoliposomes, and fragments thereof.

51. The method of claim 1, wherein the step of measuring includes applying an electrical potential difference across the at least a portion of the sample; and measuring the current necessary for maintaining the applied electrical potential difference.

52. The method of claim 1, further comprising adding an agonist to the compartment containing the sample, wherein the step of measuring at least one of an electrical potential and a current is repeated before and after the step of adding the agonist.

53. The system of claim 1, wherein the seal between the sample and the carrier is tight enough so that the variance of leakage currents through the aperture during electrical measurements lies below the signals to be measured of 0.1–50 pA at $V_M=-60$ mV by a factor of 5–10.

54. A method for analyzing membranous samples, comprising:
    selecting a measuring arrangement, comprising:
        (i) a carrier having at least one aperture,
        (ii) at least two fluid compartments, separated by the carrier, each fluid compartment connected to at least one of the other fluid compartments via at least one of the apertures, and
        (iii) at least two electrodes, each electrode being in electrical contact with at least one of the fluid compartments;
    introducing a sample into one of the fluid compartments;
    applying a voltage between at least two of the electrodes to generate an electric field in the compartment containing the sample;
    moving the sample onto the aperture, under the influence of the electric field;
    sealing the sample across the aperture;
    adding a proteoliposome to the fluid compartment containing the sample;
    fusing the proteoliposome with the sample; and
    measuring at least one of an electrical potential and a current across at least a portion of the sample, after the sample is moved to and sealed across the aperture.

55. The method of claim 54, wherein the step of fusing the proteoliposome with the sample makes membrane proteins associated with the proteoliposome accessible to electrical or optical measurements.

56. The method of claim 54, further comprising incorporating membrane proteins into the sample, after the sample is moved to the aperture.

57. The method of claim 56, wherein the membrane proteins are selected from the group consisting of ligand-controlled and G-protein-coupled receptors.

58. The method of claim 54, further comprising replacing a solution in at least one fluid compartment with another solution.

59. The method of claim 54, further comprising adding a substance to be analyzed to a solution in at least one fluid compartment.

60. The method of claim 54, further comprising carrying out an optical measurement on the sample.

61. The method of claim 60, wherein the optical measurement is a fluorescence measurement.

62. The method of claim 54, the measuring arrangement including at least two apertures and at least three fluid compartments, further comprising repeating the steps of introducing, applying, moving, sealing, and adding, such that two samples are sealed across a corresponding two apertures in the measuring arrangement.

63. The method of claim 62, further comprising repeating the step of measuring for each of the two samples, wherein the step of measuring is performed sequentially over the two samples.

64. The method of claim 62, further comprising repeating the step of measuring for each of the two samples, wherein the step of measuring is performed in parallel over the two samples.

65. The method of claim 62, the measuring arrangement further including more than two electrodes, wherein the electrodes on one side of the carrier have a common electrical potential.

66. The method of claim 62, the measuring arrangement further including more than two electrodes, wherein the electrodes on one side of the carrier are combined to form one electrode.

67. The method of claim 62, the measuring arrangement further including more than two electrodes, wherein at least one electrode serves for measurement over more than one aperture.

68. The method of claim 62, measuring arrangement having more than one aperture and twice as many electrodes as apertures, wherein there is always one aperture between two electrodes.

69. The method of claim 54, further comprising adding, exchanging, or regulating fluid or samples on one or both sides of the carrier with the aid of a pump system.

70. The method of claim 54, further comprising adding, exchanging, or regulating fluid or samples on one or both sides of the carrier with the aid of hydrostatic pressure.

71. The method of claim 54, further comprising adding, exchanging, or regulating fluid or samples on one or both sides of the carrier with the aid of a contact transfer method.

72. The method of claim 54, further comprising adding, exchanging, or regulating fluid or samples on one or both sides of the carrier with the aid of an electro-osmotic method.

73. The method of claim 54, further comprising adding, exchanging, or regulating fluid or samples on one or both sides of the carrier with the aid of at least one of a piezo drop method, an ink jet method, and a temperature-controlled method.

74. The method of claim 54, further comprising checking the fluid level in at least one compartment.

75. The method of claim 74, wherein the step of checking is performed continuously or regularly.

76. The method of claim 74, further comprising correcting the fluid level corresponding to a preset filling parameter.

77. The method of claim 54, further comprising modifying at least one of the sample and the carrier to enhance binding between the sample and the carrier.

78. The method of claim 77, wherein the step of modifying includes treating at least one of the sample and the carrier to enhance electrostatic interactions.

79. The method of claim 77, wherein the step of modifying includes treating at least one of the sample and the carrier to enhance molecule-specific interactions.

80. The method of claim 77, wherein the step of modifying includes treating at least one of the sample and the carrier to enhance multivalent-ion-mediated interactions.

81. The method of claim 80, wherein the step of treating includes adding $Ca^{2+}$ to the sample medium.

82. The method of claim 77, wherein the step of modifying includes treating at least one of the sample and the carrier to enhance hydrophilic/hydrophobic interactions.

83. The method of claim 54, further comprising cleaning the carrier in a plasma, before the step of introducing a sample.

84. The method of claim 54, further comprising the step of purifying the sample prior to the steps of adding a sample and applying an electrical potential difference.

85. The method of claim 84, wherein the step of purifying the sample includes separating members of the sample according to size.

86. The method of claim 54, wherein the step of introducing a sample further includes introducing the sample into the compartment through an inlet opening arranged above the aperture.

87. The method of claim 54, wherein the step of moving the sample further includes moving the sample to near the aperture by at least one of convection and sedimentation.

88. The method of claim 54, wherein the step of moving the sample further includes moving the sample electrophoretically.

89. The method of claim 54, wherein the carrier is electrically insulating.

90. The method of claim 54, wherein the carrier is formed at least in part of plastic.

91. The method of claim 54, wherein the carrier is formed at least in part of silicon.

92. The method of claim 91, wherein the carrier includes an applied oxide or oxynitride layer.

93. The method of claim 54, wherein the carrier is formed at least in part of glass.

94. The method of claim 54, wherein the voltage applied between the electrodes during the step of applying a voltage is in a range between about −200 mV and about +200 mV.

95. The method of claim 54, wherein the step of applying a voltage leads to the development of an inhomogeneous electric field in the compartment containing the sample.

96. The method of claim 95, wherein the inhomogeneous electric field is larger closer to the aperture than farther from the aperture.

97. The method of claim 54, wherein the strength of the electric field generated during the step of applying a voltage is at least about 100 V/m adjacent the aperture.

98. The method of claim 54, wherein the sample is selected from the group consisting of cells, biological organelles, and fragments thereof.

99. The method of claim 54, wherein the sample is selected from the group consisting of vesicles, proteoliposomes, and fragments thereof.

100. The method of claim 54, wherein the step of measuring includes applying an electrical potential difference across the at least a portion of the sample; and measuring the current necessary for maintaining the applied electrical potential difference.

101. The method of claim 54, further comprising adding an agonist to the compartment containing the sample, wherein the step of measuring at least one of an electrical potential and a current is repeated before and after the step of adding the agonist.

102. The system of claim 54, wherein the seal between the sample and the carrier is tight enough so that the variance of leakage currents through the aperture during electrical measurements lies below the signals to be measured of 0.1–50 pA at $V_M = -60$ mV by a factor of 5–10.

103. A method for analyzing membranous samples, comprising:

selecting a measuring arrangement, comprising:
(i) a carrier having at least one aperture,
(ii) at least two fluid compartments, separated by the carrier, each fluid compartment connected to at least one of the other fluid compartments via at least one of the apertures, and
(iii) at least two electrodes, each electrode being in electrical contact with at least one of the fluid compartments;

introducing a sample into one of the fluid compartments;

applying a voltage between at least two of the electrodes to generate an electric field in the compartment containing the sample;

moving the sample onto the aperture, under the influence of the electric field;

sealing the sample across the aperture;

incorporating membrane proteins into the sample, after the sample is moved to the aperture; and measuring at least one of an electrical potential and a current across at least a portion of the sample, after the sample is moved to and sealed across the aperture.

104. The method of claim 103, wherein the membrane proteins are selected from the group consisting of ligand-controlled and G-protein-coupled receptors.

105. The method of claim 103, further comprising replacing a solution in at least one fluid compartment with another solution.

106. The method of claim 103, further comprising adding a substance to be analyzed to a solution in at least one fluid compartment.

107. The method of claim 103, further comprising carrying out an optical measurement on the sample.

108. The method of claim 107, wherein the optical measurement is a fluorescence measurement.

109. The method of claim 103, the measuring arrangement including at least two apertures and at least three fluid compartments, further comprising repeating the steps of introducing, applying, moving, sealing, and adding, such that two samples are sealed across a corresponding two apertures in the measuring arrangement.

110. The method of claim 109, further comprising repeating the step of measuring for each of the two samples, wherein the step of measuring is performed sequentially over the two samples.

111. The method of claim 109, further comprising repeating the step of measuring for each of the two samples, wherein the step of measuring is performed in parallel over the two samples.

112. The method of claim 109, the measuring arrangement further including more than two electrodes, wherein the electrodes on one side of the carrier have a common electrical potential.

113. The method of claim 109, the measuring arrangement further including more than two electrodes, wherein the electrodes on one side of the carrier are combined to form one electrode.

114. The method of claim 109, the measuring arrangement further including more than two electrodes, wherein at least one electrode serves for measurement over more than one aperture.

115. The method of claim 109, the measuring arrangement having more than one aperture and twice as many electrodes as apertures, wherein there is always one aperture between two electrodes.

116. The method of claim 103, further comprising adding, exchanging, or regulating fluid or samples on one or both sides of the carrier with the aid of a pump system.

117. The method of claim 103, further comprising adding, exchanging, or regulating fluid or samples on one or both sides of the carrier with the aid of hydrostatic pressure.

118. The method of claim 103, further comprising adding, exchanging, or regulating fluid or samples on one or both sides of the carrier with the aid of a contact transfer method.

119. The method of claim 103, further comprising adding, exchanging, or regulating fluid or samples on one or both sides of the carrier with the aid of an electro-osmotic method.

120. The method of claim 103, further comprising adding, exchanging, or regulating fluid or samples on one or both sides of the carrier with the aid of at least one of a piezo drop method, an ink jet method, and a temperature-controlled method.

121. The method of claim 103, further comprising checking the fluid level in at least one compartment.

122. The method of claim 121, wherein the step of checking is performed continuously or regularly.

123. The method of claim 121, further comprising correcting the fluid level corresponding to a preset filling parameter.

124. The method of claim 103, further comprising modifying at least one of the sample and the carrier to enhance binding between the sample and the carrier.

125. The method of claim 124, wherein the step of modifying includes treating at least one of the sample and the carrier to enhance electrostatic interactions.

126. The method of claim 124, wherein the step of modifying includes treating at least one of the sample and the carrier to enhance molecule-specific interactions.

127. The method of claim 124, wherein the step of modifying includes treating at least one of the sample and the carrier to enhance multivalent-ion-mediated interactions.

128. The method of claim 127, wherein the step of treating includes adding $Ca^{2+}$ to the sample medium.

129. The method of claim 124, wherein the step of modifying includes treating at least one of the sample and the carrier to enhance hydrophilic/hydrophobic interactions.

130. The method of claim 103, further comprising cleaning the carrier in a plasma, before the step of introducing a sample.

131. The method of claim 103, further comprising the step of purifying the sample prior to the steps of adding a sample and applying an electrical potential difference.

132. The method of claim 131, wherein the step of purifying the sample includes separating members of the sample according to size.

133. The method of claim 103, wherein the step of introducing a sample further includes introducing the sample into the compartment through an inlet opening arranged above the aperture.

134. The method of claim 103, wherein the step of moving the sample further includes moving the sample to near the aperture by at least one of convection and sedimentation.

135. The method of claim 103, wherein the step of moving the sample further includes moving the sample electrophoretically.

136. The method of claim 103, wherein the carrier is electrically insulating.

137. The method of claim 103, wherein the carrier is formed at least in part of plastic.

138. The method of claim 103, wherein the carrier is formed at least in part of silicon.

139. The method of claim 138, wherein the carrier includes an applied oxide or oxynitride layer.

140. The method of claim 103, wherein the carrier is formed at least in part of glass.

141. The method of claim 103, wherein the voltage applied between the electrodes during the step of applying a voltage is in a range between about −200 mV and about +200 mV.

142. The method of claim 103, wherein the step of applying a voltage leads to the development of an inhomogeneous electric field in the compartment containing the sample.

143. The method of claim 142, wherein the inhomogeneous electric field is larger closer to the aperture than farther from the aperture.

144. The method of claim 103, wherein the strength of the electric field generated during the step of applying a voltage is at least about 100 V/m adjacent the aperture.

145. The method of claim 103, wherein the sample is selected from the group consisting of cells, biological organelles, and fragments thereof.

146. The method of claim 103, wherein the sample is selected from the group consisting of vesicles, proteoliposomes, and fragments thereof.

147. The method of claim 103, wherein the step of measuring includes applying an electrical potential difference across the at least a portion of the sample; and measuring the current necessary for maintaining the applied electrical potential difference.

148. The method of claim 103, further comprising adding an agonist to the compartment containing the sample, wherein the step of measuring at least one of an electrical potential and a current is repeated before and after the step of adding the agonist.

149. The system of claim 103, wherein the seal between the sample and the carrier is tight enough so that the variance of leakage currents through the aperture during electrical measurements lies below the signals to be measured of 0.1–50 pA at $V_M$=−60 mV by a factor of 5–10.

* * * * *